(12) United States Patent
Chaisson

(10) Patent No.: US 9,165,109 B2
(45) Date of Patent: Oct. 20, 2015

(54) SEQUENCE ASSEMBLY AND CONSENSUS SEQUENCE DETERMINATION

(75) Inventor: Mark Chaisson, San Francisco, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 755 days.

(21) Appl. No.: 13/334,601

(22) Filed: Dec. 22, 2011

(65) Prior Publication Data
US 2012/0330566 A1 Dec. 27, 2012

Related U.S. Application Data

(63) Continuation-in-part of application No. 13/034,233, filed on Feb. 24, 2011, now abandoned.

(60) Provisional application No. 61/307,732, filed on Feb. 24, 2010.

(51) Int. Cl.
G06F 19/22 (2011.01)
G06F 19/24 (2011.01)

(52) U.S. Cl.
CPC ............... *G06F 19/22* (2013.01); *G06F 19/24* (2013.01)

(58) Field of Classification Search
None
See application file for complete search history.

(56) References Cited

PUBLICATIONS

Brudno et al. LAGAN and Multi-LAGAN: Efficient tools for Large-Scale Multiple Alignment of Genomic DNA. Genome Research vol. 13, pp. 721-731 (2003).*
Abouelhoda et al. 2002 The Enhanced Suffix Array and Its Applications to Genome Analysis. Lecture Notes in Computer Sciences vol. 2452 pp. 449-463 (2002).*
Abouelhoda et al. 2005 Chaining algorithms for multiple comparison. Journal of Discrete Algorithms vol. 3, pp. 321-341 (2005).*
Morgenstern A Simple and Space-Efficient Fragment-Chaining Algorithm for Alignment of DNA and Protein Sequences. Applied Mathematics Letters vol. 15, pp. 11-16 (2002).*
Paten et al. Enredo and Pecan: Genome-wide mammalian consistency-based multiple alignments with paralogs. Genome Research vol. 18 pp. 1814-1828 (2008).*
Shendure et al. Next-generation DNA sequencing. Nature Biotechnology vol. 26, pp. 1135-1145 (2008).*
Benjamini, et al. (1995) "Controlling False Discovery Rate: a Practical and Powerful Approach to Multiple Testing," J. R. Statist. Cos. b 57, 289-300.
Bloom, et al. (1970) "Space/time trade-offs in hash coding with allowable errors," Communications of the ACM 13 (7):A22-426.
Burkhardt, et al. (2002) "One-gapped q-gram filters for Levenshtein distance," Proceedings of the 13th Symposium on Combinatorial Pattern Matching 2373: 225-234.
Chevreux, et al. (1999) "Genome Sequence Assembly Using Trace Signals and Additional Sequence Information," Intelligent Systems in Molecular Biology (ISMB) Heidelberg, Germany.
DiGuistini, et al. (2009) "De novo genome sequence assembly of a filamentous fungus using Sanger, 454 and Illumine sequence data," Genome Biology 10:R94.1-R94.12.
Farach-Colton, et al. (2007) "Optimal spaced seeds for faster approximate string matching," Journal of Computer and System Sciences 73:1035-1044.
Gusfield, et al. (1997) Algorithms on strings, trees, and sequences, Cambridge University Press, New York, NY, pp. 89-93, 421, 422.
Jeong, et al. (2008) An optimized strategy for genome assembly of Sanger/pyrosequencing hybrid data using available software, Genomics & Informatics 6(2):87-90.
Kim, et al. (1994) "Multiple sequence alignment using simulated annealing," Comput. Applic. Biosci. 10:419-426.
Kirkpatrick, et al. (1983) "Optimization by Simulated Annealing," Science, New Series 220(4598):671-680.
Koren, et al. (2007) "Autocorrelation analysis reveals widespread spatial biases in microarray experiments," BMC Genomics 8: 164.
Li, et al. (2010) "Fast and accurate long-read alignment with Burrows-Wheeler transform," Bioinformatics, 26, 589-595.
Malde, et al. (2009) "Using Bloom filters for large scale gene sequence analysis in Haskell," Proceedings of the 11th International Symposium on Practical Aspects of Declarative Languages, ISBN: 978-3-540-92994-9.
Navarro, G. (2001) "A guided tour to approximate string matching," ACM Computing Surveys 33: 31-88.
Notredame, et al. (1996) "SAGA: sesequence alignment by genetic algorithm," Nuc. Ac. Res. 24:1515-1524.
Parker, et al. (2006) "Gradient Boosting for Sequence Alignment," Proceedings of the 21st National Conference on Artificial Intelligence, pp. 452-457.
Pop, et al. (2004) "Shotgun Sequence Assembly," Advances in Computers 60, 193-248.
Reinhardt, et al. (2009) "De novo assembly using low-coverage short read sequence data from the rice pathogen *Pseudomonas syringae* pv. oryzae," Genome Res. 19:294-305.
Salvador, et al. (2004) "FastDTW: Toward Accurate Dynamic Time Warping in Linear Time and Space," KDD Workshop on Mining Temporal and Sequential Data, pp. 70-80, 2004.
Vlachos, et al. (2005) "On periodicity detection and structural periodic similarity," Proceedings of the 2005 SIAM International Conference on Data Mining, p. 449-460.
Wang, et al. (2005) "Genomic multiple sequence alignments: refinement using a genetic algorithm," BMC Bioinformatics 6:200.
Scheibye-Alsing, et al., "Sequence Assembly," Division of Genetics and Bioinformatics, IBHV, University of Copenhagen, Denmark, Drafted Apr. 27, 2009, p. 1-35.
Chaisson, et al. (2008) "Short Read Fragment Assembly of Bacterial Genomes," Genome Research 18:324-330.
Krishnamurthy, et al. (2007) "Biosequence Similarity Search on the Mercury System," Journal of VLSI Signal Processing 49:101-121.
Zerbino, et al. (2008) "Algorithms for De Novo Short Read Assembly Using de Brujin Graphs," Genome Research 18:821-829.

\* cited by examiner

*Primary Examiner* — John S Brusca
(74) *Attorney, Agent, or Firm* — Morgan, Lewis & Bockius LLP

(57) ABSTRACT

Computer implemented methods, and systems performing such methods for processing signal data from analytical operations and systems, and particularly in processing signal data from sequence-by-incorporation processes to identify nucleotide sequences of template nucleic acids and larger nucleic acid molecules, e.g., genomes or fragments thereof. In particularly preferred embodiments, nucleic acid sequences generated by such methods are subjected to de novo assembly and/or consensus sequence determination.

13 Claims, 17 Drawing Sheets

Results of Assembling DX1

| Assembly | # Contigs | Total Bases in Contigs (bp) | Max Contig Length (bp) | Total Bases in Contigs > 5kb (bp) | Mean Contig Length (bp) | N50 (bp) |
|---|---|---|---|---|---|---|
| Illumina | 193 | 5,649,046 | 189,045 | 5,543,080 | 26,259 | ? |
| PacBio-Illumina | 117 | 5,679,376 | 263,733 | 5,623,863 | 48,541 | ? |
| Sanger | 53 | 5,372,418 | 669,237 | 5,360,729 | 101,366 | ? |

| Assembly | Num | Sum | Max | Bp in contigs>5kb | Mean Contig Length (bp) | N50 (bp) |
|---|---|---|---|---|---|---|
| Illumina, un-scaffolded | 6,601 | 5,356,874 | 21,495 | 484,044 | 811 | 1,624 |
| PacBio+Illumina un-scaffolded | 2,946 | 5,811,701 | 52,130 | 3,322,537 | 1,972 | 6,129 |

Figure 15

SEQUENCE ASSEMBLY AND CONSENSUS SEQUENCE DETERMINATION

CROSS-REFERENCE TO RELATED APPLICATIONS

This application is a continuation-in-part of U.S. patent application Ser. No. 13/034,233, filed Feb. 24, 2011, which claims the benefit of U.S. Provisional Application No. 61/307,732, filed Feb. 24, 2010, the full disclosures of which are incorporated herein by reference in their entirety for all purposes.

STATEMENT REGARDING FEDERALLY SPONSORED RESEARCH

Not Applicable.

BACKGROUND OF THE INVENTION

Analysis of the subtleties of the voluminous amounts of genetic information will continue to have profound effects on the personalization of medicine. For example, this advanced genetic knowledge of patients has and will continue to have broad impact on the ability to diagnose diseases, identify predispositions to diseases or other genetically impacted disorders, and identify reactivity to given drugs or other treatments, whether adverse or beneficial.

Before one can begin to interpret genetic data from patients, one must first obtain the genetic information from that patient. Technologies have been developed that allow for broad screening of large swaths of a patient's genetic code by identifying key signposts in that code and using this fragmented data as a general interpretation mechanism, e.g., using libraries of known genetic variations, such as SNPs or other polymorphisms, and correlating the profile of such variations against profiles that have a suspected association with a given disease or other phenotype.

Rather than rely upon disparate pieces of information from the genetic code, it would be of far more value to be able to rely upon the entire text of a patient's genetic code in making any interpretations from that code. In using an analogy of a novel, one gains a substantially deeper understanding of all the elements of the novel, e.g., plot, characters, setting etc., by reading the entire text, rather than by picking out individual words from disparate pages or chapters of the novel.

Technologies related to analysis of biological information have advanced rapidly over the past decade. In particular, with the improved ability to characterize genetic sequence information, identify protein structure, elucidate biological pathways, and manipulate any or all of these, has come the need for improved abilities to derive and process this information.

In the field of genetic analysis, for example, faster and faster methods of obtaining nucleic acid sequence information have consequences in terms of requiring different and often times better methods and processes for processing the raw genetic information that is generated by these processes. This progress has been evidenced in the improvements applied to separations based Sanger sequencing, where improvements in throughput and read-length have come not only through multiplexing of multi-capillary systems, but also from improvements in base calling processes that are applied to the data derived from the capillary systems. With shifts in the underlying technology surrounding genetic analysis, also comes a necessity for a shift in the methods and processes for processing the information from these systems.

The present invention provides solutions to these and other problems.

In a resequencing study, a researcher gains insight for a biological question by comparing how the sequence of a sample differs from a reference genome. The positions in the genome where the differences occur are typically not known, and may be detected by randomly sequencing small fragments of the sample and comparing them to the reference, a method known as shotgun resequencing. The locations of the randomly sequenced fragments are not known, so an initial step in resequencing is to align the reads to their homologous locations on the reference genome.

Since the sample genome has mutations and reads have errors, homology is typically defined as the most similar sequence in the reference to the read and formulated as the highest scoring local alignment. This may be simply found with Smith-Waterman alignment (Smith, et al. (1981) J. Mol. Biol. 147:194-197); however, this is computationally prohibitive, so heuristics are necessary. A successful heuristic is sensitive to genomic variation and sequencing error; as sequencing methods have changed methods for aligning reads have evolved in step. Initial resequencing projects, such as the International Hap Map Project (Nature 409:31-46 (2001)), used Sanger sequencing (Sanger, et al. (1977) Proc. Natl. Acad. Sci. 74:5463-5467). The instrument frequently used for Sanger sequencing, the ABI 3730, produces reads roughly 1000 bases long with an accuracy over 99.5% that are rapidly aligned using MEGABLAST [25], cross match [11], and/or BLAT [14]. Each of these methods employ a Seed-and-Extend heuristic search, where short, 8-11 base, exact matches (words) are found using a hash table of the genome, and a detailed alignment is performed around regions that contain a sufficiently high number of exact matches. With reads of several hundred bases that are highly accurate, this is sufficient for aligning reads from sample genomes within the 0-1% range of common human genetic variation.

The methods developed to align reads produced by Sanger sequencing do not perform well on reads produced by Second-Generation massively parallel sequencing platforms such as the Illumina HiSeq (San Diego, Calif., USA) and Life SOLiD (Foster City, Calif., USA). Both platforms read bases four orders of magnitude faster than the state of the art in Sanger sequencing; however the reads have lower accuracy, and shorter length: 100 bases in the Illumina HiSeq and 75 bases in SOLiD 4. These platforms use the technique of amplified and cycled (AC) sequencing where millions of short templates are amplified while kept spatially separate, and then sequenced in controlled cycles of base interrogating reactions and imaging (Margulies, et al. (2005) Nature 437: 376-380; Bentley, et al. (2008) Nature 456:53-59).

The initial methods developed for aligning AC sequenced reads such as Eland (Illumina), SOAP (Li, et al. (2009) Bioinformatics 25:1966-1967), and MAQ (Li, et al. (2008) Genome Research 18:1851-1858) were based on hashing methods but achieved much faster performance than MEGA-BLAST or BLAT by bounding the number of differences allowed in a match between a read and the genome. A major algorithmic breakthrough for aligning AC reads was developed in the Bowtie alignment program (Langmead, et al. (2009) Genome Biology 10:R25) by using the Burrows-Wheeler Transformation (BWT) with a Ferrangina-Manzini (FM) index (Ferragina, et al. (2000) In Proc. of the 41st IEEE Symposium on Foundations of Computer Science, pages 390-398) of a genome rather than hash tables to detect matches between a read and a genome. The BWT-FM index, described in detail below, supports $O(Q)$ time queries for counting the number of times a query string is present in a target, where Q is the length of the query string. Reads that map to the genome without differences are found very quickly, and reads that have low error rates in the 5' end may have their prefix mapped to a very small number of candidate positions in the genome before scoring each alignment (Li, et al. (2008) Genome Research 18:1851-1858). As a result, the Bowtie method was one to two orders of magnitude faster than hash-based methods (Langmead, et al. (2009) Genome Biology 10:R25). Other mapping algorithms such as Maq and SOAP were revised to run queries using BWT-FM indices as well, with similar speedup (Li, et al. (2009) Bioinformatics 25:1754-1760; Li, et al. (2009) Bioinformatics 25:1966-1967). These methods have been robust in aligning data produced by recent updates of AC sequencing instruments, which have doubled the length of reads and increased throughput by nearly two orders of magnitude since the BWT-FM based methods were introduced.

Advances in isolation and imaging of single molecules have facilitated the development of methods for sequencing single molecules. The Pacific Biosciences® Single-Molecule Real-Time (SMRT®) sequencing platform produces reads by detecting fluorescently labeled nucleotides as a template sequence is replicated by DNA polymerase (Korlach, et al. (2008) Nucleosides, Nucleotides and Nucleic Acids 27:1072-1083; Eid, et al. (2009) Science 323:133-138; Levene, et al. (2003) Science 299: 682-686, the disclosures of which are incorporated herein by reference in their entireties for all purposes). The polymerase and template are bound to the bottom of a zero-mode waveguide (ZMW) that limits the detection volume to the zeptoliter scale allowing the signal from the incorporated nucleotides to be distinguished from the background signal of nucleotides in solution. An alternative method has been shown to detect bases that have been cleaved by endonuclease and pass through a protein nanopore by monitoring modulations of ionic current across the pore (Clarke, et al. (2009) Nature Nanotechnology 4:265-270, incorporated herein by reference in its entirety for all purposes). Finally, a method has been recently demonstrated for identifying bases that have translocated through a nanopore fabricated in a graphene membrane (Garaj, et al. (2010) Nature 467:190-193). The mapping methods written for AC sequencing reads will likely not work well on SMS reads, and older alignment methods such as Blast will be too slow. Thus there is a need for the development of new mapping methods for single molecule sequencing reads.

BRIEF SUMMARY OF THE INVENTION

The invention is generally directed to methods, systems, and compositions, and particularly computer-implemented processes for analyzing sequence data. In certain embodiments, the invention is particularly useful for analyzing biomolecular sequence data, e.g., amino acid or nucleic acid sequence data. Nucleic acid sequence data generated during template-directed sequencing reactions is particularly suitable for use with the invention, e.g., for ultimately identifying sequence information of a target nucleic acid sequence. Consequently, the invention is also directed to devices and systems that carry out these processes.

The invention and various specific aspects and embodiments will be understood with reference to the following drawings and detailed descriptions. In some of the drawings and detailed descriptions below, the present invention is described in terms of an important independent embodiment of a system operating on a logic processing device, such as a computer system. This should not be taken to limit the invention, which, using the teachings provided herein, can be applied to any number of logic processors working together, whether incorporated into a camera, a detector, other optical components, or other information enabled devices or logic components incorporated into laboratory or diagnostic equipment or in functional communication therewith. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims.

Furthermore, it is well known in the art that logic systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification. The functional aspects of the invention that are implemented on a computer or other logic processing systems or circuits, as will be understood from the teachings herein, may be implemented or accomplished using any appropriate implementation environment or programming language, such as C, C++, Cobol, Pascal, Java, Java-script, HTML, XML, dHTML, assembly or machine code programming, RTL, etc. All references, publications, patents, and patent applications cited herein are hereby incorporated by reference in their entirety for all purposes.

Methods for de novo assembly of a bacterial genome using reads from Pacific Biosciences' single-molecule real-time (SMRT™) DNA sequencing technology are described. This sequencing approach uses an iterative overlap-layout-consensus method generally based on the AMOS assembly software package and employs several novel algorithms tailored to long reads, e.g., such as that produced by Pacific Biosciences™ Single-Molecule Real-Time (SMRT™) sequencing methods and systems.

Methods are provided for performing overlap detection. For example, use of a greedy algorithm on a suffix tree that allows a wide-range of specific matches and errors, providing substantial flexibility and sensitivity in overlapping reads of widely disparate lengths and error patterns (e.g. hybrid assembly of long reads from one sequencing platform with short reads from a different platform) is described. For example, methods are provided to facilitate identification of overlap regions in sequence data having high insertion and deletion rates relative to substitution rates, e.g., using modified k-mer error models and/or modified suffix tree query algorithms. A parallelized version of the AMOS layout algorithm tigger, and a consensus algorithm which employs a probabilistic graphical model to represent the error characteristics of long reads are also described herein.

In addition, methods for further refining a sequence alignment construct are provided. In certain embodiments, simulated annealing and nontraditional objective functions are used for alignment refinement. In other embodiments, alignment refinement comprises the use of global chaining in combination with sparse dynamic programming.

Certain aspects of the present invention provide methods, e.g., computer-implemented methods, of identifying regions of sequence overlap between a plurality of sequencing reads.

In certain embodiments, such methods comprise providing the plurality of sequencing reads within a data structure; generating a set of k-mers having deletions and/or insertions; searching the data structure for regions of the sequencing reads that match a first k-mer of the set of k-mers, wherein the regions are identified as regions of sequence overlap between the sequencing reads; and searching the data structure with further k-mers in the set of k-mers to identify further regions of sequence overlap between the sequencing reads. In some cases, the set of k-mers can include both deletion-comprising k-mers and insertion-comprising k-mers, k-mers having multiple deletions, k-mers having multiple insertions, k-mers having substitutions, or combinations thereof. In specific embodiments, the set of k-mers has a combined insertion-deletion rate of 5-20%. The set of k-mers can be stored and/or searched for in a data structure, e.g., a hash table, a suffix tree, a suffix array, or a sorted list. In some embodiments, the data structure is searched using a greedy algorithm modified to allow for k-mers having mutations, such as insertions, deletions, and substitutions, and in other embodiments it is searched using an O(N) algorithm comprising Bloom filters, which can optionally store the set of k-mers. Providing the sequencing reads preferably comprises performing at least one sequencing-by-incorporation assay, which may be performed in a confined reaction volume, such as a zero-mode waveguide. Redundant sequencing methods, including resequencing and sequencing multiple copies of a template molecule, can be used to generate the sequencing reads. Optionally, the sequencing reads can be filtered, e.g., before being included in the data structure, and such filtering can be performed on the basis of various criteria including, but not limited to, read quality and call quality. In certain preferred embodiments, one or more of the plurality of sequencing reads, the data structure, the set of k-mers, the regions of sequence overlap, and the further regions of sequence overlap is stored on a computer-readable medium and/or displayed on a screen.

Some aspects of the invention provide methods, e.g., computer-implemented methods, for identifying regions of sequence overlap between a plurality of sequencing reads. Such methods typically comprise providing the plurality of sequencing reads within a data structure; generating a set of k-mers; searching the data structure for regions of the sequencing reads that match a first of the set of k-mers, wherein the regions are identified as regions of sequence overlap between the sequencing reads, and further wherein the searching is performed using an O(N) algorithm comprising Bloom filters; and repeating the searching with further k-mers in the set of k-mers to identify further regions of sequence overlap between the sequencing reads. In some cases, the set of k-mers can include both deletion-comprising k-mers and insertion-comprising k-mers, k-mers having multiple deletions, k-mers having multiple insertions, k-mers having substitutions, or combinations thereof. In specific embodiments, the set of k-mers has a combined insertion-deletion rate of 5-20%. The set of k-mers can be stored and/or searched for in a data structure, e.g., a hash table, a suffix tree, a suffix array, a sorted list, or in the Bloom filters. Providing the sequencing reads preferably comprises performing at least one sequencing-by-incorporation assay, which may be performed in a confined reaction volume, such as a zero-mode waveguide. Redundant sequencing methods, including resequencing and sequencing multiple copies of a template molecule, can be used to generate the sequencing reads. Optionally, the sequencing reads can be filtered, e.g., before being included in the data structure, and such filtering can be performed on the basis of various criteria including, but not limited to, read quality and call quality. In certain preferred embodiments, one or more of the plurality of sequencing reads, the data structure, the set of k-mers, the regions of sequence overlap, and the further regions of sequence overlap is stored on a computer-readable medium and/or displayed on a screen.

In yet further aspects, the invention provides methods, (e.g., computer-implemented methods) for identifying regions of sequence overlap between sequencing contigs, some embodiments of which include deriving a plurality of first sequencing contigs from a first plurality of sequencing reads from a first sequencing method; deriving a second plurality of second sequencing contigs from a second plurality of sequencing reads from a second sequencing method, wherein the first and second sequencing methods are different from one another; incorporating the first sequencing contigs and the second sequencing contigs into a data structure; generating a set of k-mers; searching the data structure for regions of the sequencing contigs that match a first k-mers of the set of k-mers, wherein the regions are identified as regions of sequence overlap between the first sequencing contigs and the second sequencing contigs; and repeating the searching with further k-mers in the set of k-mers to identify further regions of sequence overlap between the first sequencing contigs and the second sequencing contigs. The set of k-mers is optionally stored or searched for in a data structure, e.g., a hash table, a suffix tree, a suffix array, or a sorted list. The data structure can be searched using various algorithms, e.g., a greedy algorithm or an O(N) algorithm comprising Bloom filters, which can optionally store the set of k-mers. At least one of the first or second sequencing method is preferably a sequencing-by-incorporation method. In some embodiments, at least one of the sequencing contigs, the data structure, the set of k-mers, the regions of sequence overlap, and the further regions of sequence overlap is stored on a computer-readable medium and/or is displayed on a screen. In specific embodiments, the first plurality of sequencing reads are long, optionally contiguous, sequencing reads and the second plurality of sequencing reads are short or paired-end sequencing reads. Certain methods for identifying regions of sequence overlap between sequencing contigs further comprise deriving a plurality of third sequencing contigs from a third plurality of sequencing reads from a third sequencing method, wherein the third sequencing method is different from the first and second sequencing methods, and incorporating the third sequencing contigs into the data structure, wherein the regions identified during the searching are regions of sequence overlap between the first sequencing contigs, the second sequencing contigs, and the third sequencing contigs. In certain embodiments, the first and second sequencing methods are selected from pyrosequencing, tSMS sequencing, Sanger sequencing, Solexa sequencing, SMRT sequencing, SOLID sequencing, Maxam and Gilbert sequencing, nanopore sequencing, and semiconductor sequencing.

Further, the present invention provides methods for aligning a sequence read to a reference sequence. In certain embodiments, such methods comprise mapping short subsequences of the sequence read to the reference sequence using a suffix array; using global chaining, identifying regions within the reference sequence to which a plurality of the subsequences of the sequence read map; scoring and remapping the regions using sparse dynamic programming; and aligning matches, e.g., using basecall quality values and at least one of a banded affine or pair-HMM, alignment. The scoring and mapping are optionally performed iteratively.

Typically, a sequence read is provided, e.g., by performing a sequencing reaction on a target nucleic acid. A reference sequence for the target nucleic acid is provided and a set of subsequences in the sequence read is identified, wherein each of the subsequences matches a portion of the reference sequence. The set of subsequences is refined, optionally iteratively, by scoring and realigning the subsequences to the reference sequence using sparse dynamic programming. A banded dynamic programming alignment, e.g., affine or Pair-HMM, is preferably used to score and realign the final set of subsequences to provide the final alignment of the sequence read to the reference sequence. In preferred embodiments, the identification of the matching subsequences comprises finding all exact matches from the sequence read that are longer than a minimum match length, k, and that match the reference sequence. Optionally, the identification of the subsequences in the sequence read that match portions of the reference sequence is performed using a suffix array or a BWT-FM index. Preferably, the identification of the subsequences in the sequence read that match portions of the reference sequence comprises clustering exact matches using global chaining. The clustering typically comprises sorting the exact matches by position within the reference sequence and within the sequence read and finding a first subset of non-overlapping exact matches that is larger than any other subset of non-overlapping exact matches, wherein the first subset is identified as a cluster and the cluster is one of the set of subsequences. In preferred embodiments, the set of subsequences is scored and ranked prior to the refining steps. Following the scoring and realigning, each iteration of the refining redetermines subsets of non-overlapping exact matches, and further identifies the largest of these subsets. In some embodiments, the banded alignment comprises aligning all bases in the sequence read to the reference sequence using alignments from the sparse dynamic programming of step d as a guide. A mapping quality value is preferably calculated, as well. Various steps of the method can be implemented on a computer, e.g., using computer-readable code, and various results or outputs from the steps can be stored on computer-readable media and/or displayed on a computer monitor.

In certain aspects, systems for generating a consensus sequence are provided. In preferred embodiments, such systems comprise computer memory comprising a sequence read for a target nucleic acid; computer memory comprising a reference sequence for the target nucleic acid; computer-readable code for finding a set of subsequences in the sequence read that match portions of the reference sequence; computer-readable code for refining the set of subsequences, wherein the refining comprises scoring and realigning the subsequences using sparse dynamic programming; computer-readable code for scoring and realigning a final set of subsequences using a banded alignment, thereby aligning the sequence read to the reference sequence; and computer memory for storing the output of at least one of the steps of the method. Optionally, the system can further comprise a monitor for displaying at least one of the sequence read, the reference sequence, and the output of at least one of the steps of the method.

In further aspects of the invention, a system for generating a consensus sequence is provided that comprises computer memory containing a set of sequence reads; computer-readable code for applying an overlap detection algorithm to the set of sequence reads and generating a set of detected overlaps between pairs of the sequence reads; computer-readable code for assembling the set of sequence reads into an ordered layout based upon the set of detected overlaps; and memory for storing the ordered layout.

In yet further aspects, the invention provides methods for identifying periodicity for a repetitive sequence read. For example, some such methods comprise calculating a self-alignment scoring matrix with a special boundary condition for the repetitive sequence read; summing over the scoring matrix to generate a plot providing accumulated matching scores over a range of base pair offsets; identifying a set of peaks in the plot having highest accumulated matching scores; determining a first base pair offset for a first peak in the set, wherein the first peak has a lower base pair offset than any of the other peaks; and identifying the periodicity for the repetitive sequence read as an amount of the first base pair offset. The methods may also include determining at least a second base pair offset for a second peak in the set, wherein the second peak has a lower base pair offset than any of the other peaks except the first peak; and further using the second base pair offset to validate the first base pair offset. In certain preferred embodiments, the periodicity for the repetitive sequence read determined by the methods herein is used during overlap detection within the repetitive sequence read.

Although specific embodiments are described herein, it is to be understood that the methods described herein may be used in combination with other methods, systems, and compositions related to nucleic acid sequence data analysis including, e.g., those described in U.S. Pat. No. 7,056,661; U.S. Patent Publication No. 2009002433; U.S. patent application Ser. No. 12/592,284, filed Nov. 20, 2009; Korlach, et al. (2008) Nucleosides, Nucleotides and Nucleic Acids 27:1072-1083; Lundquist, et al. (2008) Optics Letters 33(9): 1026; Eid, et al. (2009) Science 323:133-138; and Levene, et al., Science 299 (5607):682-686 (2003), all of which are incorporated herein by reference in their entireties for all purposes.

Further, various embodiments and components of the present invention employ pulse, signal, and data analysis techniques that are familiar in a number of technical fields. For clarity of description, details of known techniques are not provided herein. These techniques are discussed in a number of available references works, such as: R. B. Ash. Real Analysis and Probability. Academic Press, New York, 1972; D. T. Bertsekas and J. N. Tsitsiklis. Introduction to Probability. 2002; K. L. Chung. Markov Chains with Stationary Transition Probabilities, 1967; W. B. Davenport and W. L Root. An Introduction to the Theory of Random Signals and Noise. McGraw-Hill, New York, 1958; S. M. Kay, Fundamentals of Statistical Processing, Vols. 1-2, (Hardcover—1998); Monsoon H. Hayes, Statistical Digital Signal Processing and Modeling, 1996; Introduction to Statistical Signal Processing by R. M. Gray and L. D. Davisson; Modern Spectral Estimation: Theory and Application/Book and Disk (Prentice-Hall Signal Processing Series) by Steven M. Kay (Hardcover—January 1988); Modern Spectral Estimation: Theory and Application by Steven M. Kay (Paperback—March 1999); Spectral Analysis and Filter Theory in Applied Geophysics by Burkhard Buttkus (Hardcover—May 11, 2000); Spectral Analysis for Physical Applications by Donald B. Percival and Andrew T. Walden (Paperback—Jun. 25, 1993); Astronomical Image and Data Analysis (Astronomy and Astrophysics Library) by J.-L. Starck and F. Murtagh (Hardcover—Sep. 25, 2006); Spectral Techniques In Proteomics by Daniel S. Sem (Hardcover—Mar. 30, 2007); Exploration and Analysis of DNA Microarray and Protein Array Data (Wiley Series in Probability and Statistics) by Dhammika Amaratwiga and Javier Cabrera (Hardcover—Oct. 21, 2003), all of which are incorporated herein by reference in their entireties for all purposes.

BRIEF DESCRIPTION OF THE DRAWINGS

FIG. 15 provides statistics related to the assembly of the DX1 genome.

DETAILED DESCRIPTION OF THE INVENTION

I. General

Figure 1:
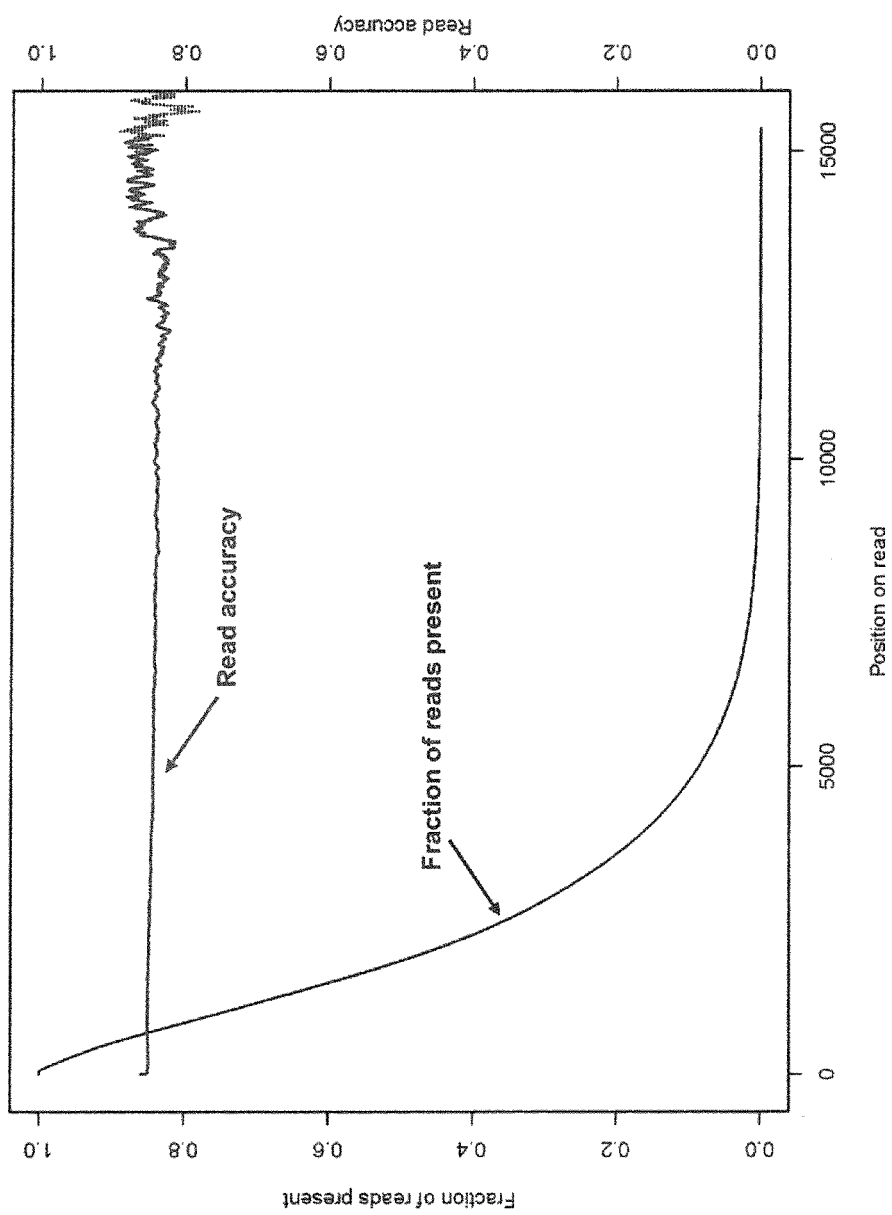
FIG. 1 provides a plot showing exemplary data from a sequencing project.

The methods presented herein are generally applicable to analysis of sequence information, and in particular the assembly of overlapping sequence data into a contig, which can be further analyzed to determine a consensus sequence. While many different type of sequence data can be analyzed using the methods and systems described herein, the invention is especially suitable for analysis of sequences of biomolecular sequences, such as nucleic acids and proteins. Methods for sequencing biomolecules have been known to those of skill in the art for many years, and more advanced techniques that increase throughput, readlength, and accuracy have been developed and commercially introduced. These advances have vastly increased the amounts of sequence data produced, as well as the need for improved sequence analysis techniques.

In certain aspects, the present invention provides methods for de novo assembly and consensus sequence determination through analysis of biomolecular (e.g., nucleic acid or polypeptide) sequence data. Typically, a first step in sequence analysis is determination of one or more sequence "reads," or contiguous orders of the molecular units or "monomers" in the sequence. For example, a nucleic acid sequencing read comprises an order of nucleotides or bases in a polynucleotide, e.g., a template molecule and/or a polynucleotide strand complementary thereto. Exemplary methods for determination of sequence reads that can be analyzed by the methods provided herein include, e.g., Sanger sequencing, shotgun sequencing, pyrosequencing (454/Roche), SOLiD sequencing (Life Technologies), tSMS sequencing (Helicos), Illumina® sequencing, and in certain preferred embodiments, single-molecule real-time (SMRT™) sequencing (Pacific Biosciences of California). These methods are well known to those of ordinary skill in the art, and each can produce sequence reads that can be aligned and assembled using methods described herein.

For each type of sequencing technology, experimental data collected during one or more sequencing reactions must be analyzed to determine one or more sequence reads for a given template nucleic acid subjected to the sequencing reaction(s). For example, pyrosequencing relies on production of light by an enzymatic reaction following an incorporation of a nucleotide into a nascent strand that is complementary to a template nucleic acid; fluorescently-labeled oligonucleotides are detected during SOLID sequencing, and fluorescently-labeled nucleotides are used in tSMS, Illumina®, and SMRT sequencing reactions. For example, in SMRT sequencing, a set of differentially labeled nucleotides, template nucleic acid, and a polymerase are present in a reaction mixture. As the polymerase processes the template nucleic acid a nascent strand is synthesized that is complementary to the template nucleic acid. The label on each nucleotide is typically and preferably linked to a portion of the nucleotide that is not incorporated into the nascent strand. The labeled nucleotides in the reaction mixture bind to the active site of the polymerase enzyme, and during the binding and subsequent incorporation of the constituent nucleoside monophosphate, the label is removed and diffuses away from the complex. For example, where the label is linked to the terminal phosphate group of the nucleotide, it is cleaved from the nucleotide by the enzymatic activity of the polymerase which cleaves the polyphosphate chain between the alpha and beta phosphates. Since detection of fluorescent signal is typically restricted to a small portion of the reaction mixture that includes the polymerase, e.g., within a zero-mode waveguide (ZMW), a series of fluorescence pulses are detectable and can be attributed to incorporation of nucleotides into the nascent strand with the particular emission detected being indicative of a specific type of nucleotide (e.g., A, G, T, or C). Further details of SMRT sequencing are provided in Korlach, et al. (2008) Nucleosides, Nucleotides and Nucleic Acids 27:1072-1083; Eid, et al. (2009) Science 323:133-138; and in U.S. Pat. Nos. 7,056,661, 7,315,019, and 6,917,726, all of which are incorporated herein by reference in their entireties for all purposes. By analyzing various characteristics of the "pulse trace," which comprises the series of detected fluorescence pulses, the sequence of nucleotides incorporated can be determined and, by complementarity, the sequence of at least a portion of the template nucleic acid is derived therefrom. The identification of the type and order of nucleotides incorporated is typically performed using computer-implemented methods, e.g., such as those described in U.S. Patent Publication No. 2009/0024331 and U.S. Provisional Application No. 61/307, 672, filed Feb. 24, 2010, the disclosures of which are incorporated herein by reference in their entireties for all purposes.

Different sequencing technologies have different inherent error profiles in the sequence reads they produce. Redundancy in the sequence data can be used to identify and correct errors in individual sequence reads. Various methods are used to produce sequence data having such redundancy. For example, the reactions can be repeated, e.g., by iteratively sequencing the same template, or by separately sequencing multiple copies of a given template. In doing so, multiple reads can be generated for one or more regions of the template nucleic acid, and preferably each read overlaps completely or partially with at least one other read in the data set produced by the redundant sequencing. Further, different regions of a template can be sequenced by using different primers to initiate sequencing in different regions of the template, and preferably the resulting sequence reads overlap to allow construction of a consensus sequence representative of the true sequence of the different regions of the template nucleic acid based upon sequence similarity between portions of different reads that overlap within those regions. Further information on strategies for generating overlapping sequence reads and redundant sequencing of nucleic acids is provided in U.S. Pat. No. 7,476,503; U.S. Patent Publication Nos. 20090298075, 20100081143, and 20100311061; and U.S. patent application Ser. No. 12/982,029, filed Dec. 30, 2010, the disclosures of which are incorporated herein by reference in their entireties for all purposes. The sequence reads for a given template sequence are assembled like a puzzle based upon sequence overlap between the reads, e.g., to form a "contig," and the alignment of the reads relative to one another provides the position of each read relative to the other reads and, preferably, relative to the template nucleic acid. In general, longer and more accurate reads facilitate contig assembly, and in some embodiments a known "reference" sequence (e.g., from a public database or repository) can also be used during construction of the contig. A region that is covered by two or more individual sequence reads having overlapping segments corresponding at least to the region can then be subjected to a more accurate sequence determination that is generally impossible using a single sequence read. The overlapping portions of the sequence reads that correspond to the region are compared or otherwise analyzed with respect to one another. In this way, erroneously called bases can be identified and, optionally corrected, in individual reads during the assembly process, and this information used to determine a more accurate consensus sequence for the region. In other words, once the alignment between separate reads is determined, a best or most likely call can be determined for each position in the overlapping portions, assigned to that position in a consensus sequence, and used to determine the most likely call for that position in the original template molecule. Certain methods for consensus sequence determination that can be used with the alignment and assembly methods provided herein are provided in U.S. Patent Publication No. 2010/0169026, the disclosure of which is incorporated herein by reference in its entirety for all purposes.

As such, correct consensus sequence determination for a template molecule is greatly facilitated by accurate alignments of the overlapping sequencing reads, which allow determination of which positions within individual reads correspond to a single position in the template sequence. However, certain sequence read characteristics can complicate alignment. For example, some sequencing technologies produce very short sequence reads, which require a very high fold-coverage to ensure the template sequence is adequately covered, and even at high fold-coverage these reads may not allow resolution of highly repetitive regions, e.g., that are longer than the typical length of the reads. Other sequencing technologies produce long sequencing reads that allow better resolution of repeat regions and facilitate assembly, but may do so at the expense of accuracy. In addition, the types of errors that characterize sequence reads must also be addressed, e.g., substitutions (e.g., misincorporation or miscalled bases) versus insertions and deletions (e.g., multiply-counted or missed bases). The present invention provides robust methods for alignment of individual sequence reads with one another, e.g., for the purposes of identifying regions of overlap between the sequence reads, which are useful in determining a highly accurate sequence of a template molecule that was subjected to the sequencing reaction. In some embodiments, different types of sequence reads can be combined into a single contig, or into a scaffold, which may include positions for which a base call has not been determined (e.g., that correspond to gaps in the raw sequence reads), which can be designated by "N" in the scaffold. For example, less accurate long sequence reads can be combined with short but highly accurate sequence reads in a process termed "hybrid assembly," as further described below. The long reads can facilitate placement of the small reads into a contig or scaffold, and the basecalls in the short reads can be given more weight in the final consensus sequence determination due to their higher inherent accuracy. As such, the advantages inherent to each type of sequence read can be used to maximize the accuracy of the resulting assembly.

Although certain aspects of the methods herein focus on an alignment of reads produced by the PacBio® RS sequencing instrument (Pacific Biosciences, Menlo Park, Calif.), the characteristics of sequences reads produced by the PacBio® RS instrument are likely to be common to other single molecule sequencing methods. The main differences in read characteristics to consider for designing alignment routines for SMS reads are that they are one to two orders of magnitude longer than AC reads, and that the sequencing errors are biased towards insertions and deletions at a higher overall error rate than that in AC sequencing. In contrast to AC methods, the signals observed in SMS do not have the problems of phasing or prephasing (Kao, et al. (2009) Genome Research 10:1884-1895) where signal is observed from different positions in an amplified template at the same cycle. Fluorescence signal does not decrease across the length of a read, allowing both longer reads and no positional bias in base calling error, as shown by the "Read accuracy" line in FIG. 1. The length of reads in the PacBio RS platform is limited by processivity of the polymerase and may be approximated by an exponential processes. The fraction of reads with length greater than or equal to a given length on the x-axis is shown by "Fraction of reads present" in FIG. 1. Base calls are derived from real-time measurements of analog fluorescence during incorporation. A small fraction of the time, bases will incorporate faster than the limit of detection, resulting in deletions in the called sequence. Other times, bases reside in the observation volume but are not incorporated into the growing strand, and give signal that result in insertions in the read. Incorrect bases are rarely incorporated, leaving a very low substitution rate. The effect of this is a bias in the type of error in SMS to insertions and deletions. The raw accuracy is lower than AC sequencing, however due to lack of positional bias in sequencing error the consensus accuracy grows quickly with coverage (Travers, et al. (2010) Nuc. Ac. Res. 38(15):e159).

In certain aspects of the methods provided herein, SMS reads having high indel rates are mapped to genomes by finding clusters of short exact matches between the read and the genome. To investigate the feasibility of doing so in the human genome, we need to determine two metrics: the number of matches of minimal length expected to exist between a read and the genome at a given sequencing accuracy and read length, and the number of false positive clusters the read is expected to have elsewhere in the genome. If the chances of finding a match between the read and the genome is low, or there are many regions a read may map to incorrectly with high identity, our proposed approach would not be feasible.

For a particular read length, and accuracy, we present a method to determine the probability of the read containing a sufficient number of anchors to map by solving a problem of counting integer compositions. We next examine the repeat structure of the human genome to determine how difficult it will be to map to due to the repetitive nature of the genome. Rather than defining repeat content as the amount of sequence sharing high percent identity, we measure a different similarity metric on the human genome, the anchor similarity, where sequences similarity is measured as the number of shared anchors between the two sequences from the genome. We found that there are both a high number of expected matches between the read and the genome, and few false positive clusters of matches of the same size elsewhere in the genome, indicating that the proposed approach would be feasible at least in the problem of mapping reads to the human genome.

Provided herein is a program called BLASR (Basic Local Alignment with Successive Refinement) that uses a combination of data structures used in short read mapping with sparse dynamic programming alignment methods (Eppstein, et al. (1992) J. Assoc. Comput. Mach. 39:519-545) used in whole genome alignment such as the LAGAN aligner (Brudno, et al. (2003) Bioinformatics, 19 Supplement 1:i54-i62). A BWT-FM index or suffix array of a genome is queried to generate short exact matches that are clustered and give approximate starting and ending coordinates in the genome for where a read should align. A more detailed alignment is generated by using sparse dynamic programming between a set of short exact matches in the read to the region it maps to, and a final detailed alignment is generated using dynamic programming within an area guided by the sparse dynamic programming alignment.

II. Algorithm Overview

In certain aspects, the invention provides methods for alignment and assembly of nucleic acid sequencing reads that comprise overlapping or redundant sequence information. The methods herein may be used in combination with other alignment and assembly methods known to those of ordinary skill in the art. For example, the overlap detection may comprise one or more alignment algorithms that align each read using a reference sequence. In some embodiments in which a reference sequence is known for the region containing the target sequence, the reference sequence can be used to produce an alignment using a variant of the center-star algorithm. Alternatively, the sequence alignment may comprise one or more alignment algorithms that align each read relative to every other read without using a reference sequence ("de novo assembly routines"), e.g., PHRAP, CAP, ClustalW, T-Coffee, AMOS make-consensus, or other dynamic programming MSAs. Additional alignment and assembly methods are described in "Assembly and Alignment Algorithms for Next-Gen Sequence Data" (December 2008/January 2009) Genome Technology; Boisvert et al., (2010) J. Comput. Biol. 17(11):1519-33; Butler et al. (2008) Genome Res. 18:810-820; Chevreux, et al. (1999) ISMB meeting, Heidelberg, Germany; DiGuistini, et al. (2009) Genome Biology 10:R94; Jeong, et al. (2008) Genomics & Informatics 6(2): 87-90; Li et al., Genome Res. published online, Aug. 19, 2008; Li et al. (2008) Bioinformatics 24:713-714; Ning et al. (2001) Genome Res. 11:1725-1729; Shendure et al. (2008) Nature Biotechnology 26:1135-1145; Sundquist et al. (2007) PLoS One 2:e484; Warren et al. (2007) Bioinformatics 23:500-501; and Zerbino et al. (2008) Genome Res. 18:821-829, the disclosures of which are incorporated herein by reference in their entireties for all purposes. Further, computer software read assemblers are now available, e.g., The TIGR Assembler (Sutton et al. (1995) Genome Science and Technology 1:9-19); GAP (Bonfield et al (1995) Nucleic Acids Res. 23:4992-4999); CAP2 (Huang et al. (1996) Genomics 33:21-31); the Genome Construction Manager (Laurence et al. (1994) Genomics 23:192-201); Bio Image Sequence Assembly Manager; SeqMan (Swindell et al. (1997) Methods Mol. Biol. 70:75-89); and LEADS and GenCarta (Compugen Ltd., Israel), which may also be used with the methods described herein.

In some embodiments, the invention provides methods for aligning and assembling sequence reads based at least in part on a known reference sequence, which is sometimes termed "resequencing" or "mapping." In such embodiments, the sequence reads can be mapped to the reference sequence, and loci that have basecalls that differ from the reference sequence can be further analyzed to determine if a given locus was erroneously called in the sequence read, or if it represents a true variation (e.g., a mutation, SNP variant, etc.) that distinguishes the nucleotide sequence of the reference sequence from that of the template nucleic acids that were sequenced to generate the sequence reads. Such variations may encompass multiple adjacent positions in the reference and/or the sequencing reads, e.g., as in the case of insertions, deletions, inversions, or translocations. As such, a sequence is assembled based upon the alignment of the reference sequence and the sequence reads that are similar but not necessarily identical to at least a portion of the reference sequence.

In related aspects, the invention provides methods for aligning and assembling sequence reads that do not use a known reference sequence, which is sometimes termed "de novo sequencing." In such applications, the sequence reads are analyzed to identify overlap regions, which are aligned to each other to generate a contig, which can be subjected to consensus sequence determination, e.g., to form a new, previously unknown sequence, such as when an organism's genome is sequenced for the first time. In general, de novo assemblies are orders of magnitude slower and more memory intensive than resequencing assemblies, mostly due to the need to analyze or compare every read with every other read, e.g., in a pair-wise fashion. Typically, in such applications the sequence reads themselves are used as "reference" in the alignment algorithms.

In certain aspects, the invention provides methods for hybrid assembly of nucleic acid sequencing reads, in particular assembly of long (e.g., those generated by Pacific Biosciences™ SMRT™ sequencing ("PacBio reads")) and short (e.g., those generated by Illumina®) nucleic acid sequencing reads. Hybrid assembly is a method by which reads from different sequencing methodologies are aligned with one another, and such alignments are useful in many contexts. While more and longer sequence reads facilitate identification of sequence overlaps, they may have higher error rates than reads from short-read technologies. Conversely, short sequence reads are faster to align, but are more difficult to align when the template from which they were generated comprises repeats (identical or near-identical) or large rearrangements, such as inversions or translocations, that are longer than the length of the short reads. Typically, longer reads from a first platform are used to form a "baseline" to which other types of reads, e.g., from short-read platforms, are added. For example, since different researchers may use different sequencing platforms, the methods herein allow sequencing data from the different platforms to be combined to provide overall higher quality data, e.g. due to higher redundancy or compensation of one or more weaknesses of one with the strengths of the other. Further, a hybrid assembly can be used to select regions of high quality reads from one platform ("A") based on the "higher quality" sequence generated by the other platform ("B"), as further described in Example I herein.

In certain preferred embodiments, the hybrid assembly methodology is used for de novo assembly. Overlaps in such hybrid assemblies can be augmented or filtered in various ways. For example, candidate overlap regions observed in the long reads can be corroborated with regions in the short reads that overlap the candidate overlap regions in the long reads. Alternatively or additionally, candidate overlap regions between long reads or long and short reads can be corroborated if they are flanked or spanned by a mate pair or strobe reads, as described elsewhere herein. Corroboration of a candidate overlap can also be accomplished by comparison to a reference sequence. In related embodiments, regions that do not align to a reference sequence can be targeted for more aggressive mis-assembly detection. In some instances, given convincing experimental sequence read data, the analysis may even override the reference sequence (which may actually contain sequence data that does not correspond to the template sequence, e.g., due to genetic variability, errors in reference sequence determination, etc.).

Figure 2:
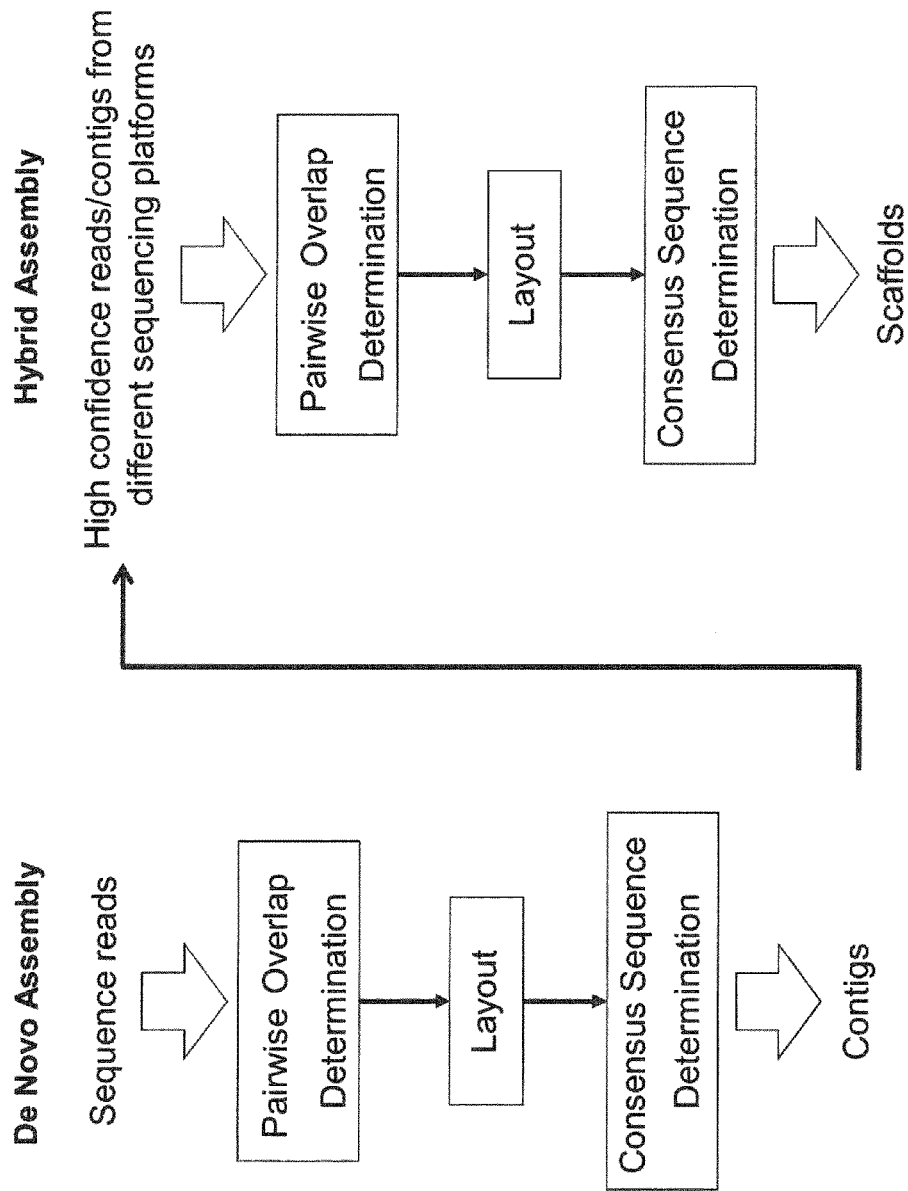
FIG. 2 provides a general overview of de novo and hybrid assembly methods, including how they are used together in certain embodiments.

FIG. 2 provides a general overview of de novo and hybrid assembly methods, including how they are used together in certain embodiments. There are three basic stages of de novo assembly. The first is overlap detection, which is typically performed in a pairwise fashion in which two sequence reads are compared and/or analyzed with respect to one another at a time, and the process continues until all sequence reads have been compared to all other sequence reads. The second stage is layout, in which the overlaps detected in the first stage are used to order all the sequence reads having such overlaps with respect to one another. The third stage is consensus sequence determination, in which positions within the overlapping regions that are different within different reads are further analyzed to determine a "best" call for the position, e.g., based upon quality scores for individual basecalls and the frequency of each type of basecall within the set of sequence reads that include that position. The process produces assembled reads, or contigs, that provide the best sequence for the template nucleic acid from which the sequence reads were derived.

Hybrid assembly comprises similar stages as does de novo assembly: overlap determination, layout, and consensus sequence determination. However, the input sequences are typically high confidence reads or contigs from multiple different sequencing technologies, e.g., short-read and long-read technologies. In preferred embodiments, the different sequencing technologies used in hybrid assembly produce sequence reads and/or contigs having different error profiles, i.e., that are characterized by different types and/or frequencies of sequencing and/or assembly errors. The process assembles the contigs (typically FASTA-formatted) from the different technologies to produce hybrid contigs or "scaffolds," which are presented as oriented contigs in a linear graph, typically in FASTA or graphml format. Depending on the types of reads used in the hybrid assembly process, the resulting linear graphs may contain ambiguous regions or gaps, e.g., where one or more positions are not covered by the assembled contigs. For example, in some cases the original sequence reads do not include the positions within the gap, and in other cases the quality of calls within the gap region is determined to be too low to include these calls in the hybrid assembly process. These ambiguous positions or gaps are typically represented by Ns in the scaffold. e.g., with each ambiguous position or basecall denoted by an "N" and a series of "N" positions for gaps spanning multiple positions. For example, certain sequencing methods, e.g., "strobe sequencing" or paired-end sequencing, produce sequence reads having gaps, and if reads from a second sequencing technology do not span those gaps then the final assembled sequence may not have a specific base call for every position. Further details of strobe sequencing, e.g., when intermittent detection is used to generate multiple, noncontiguous sequence reads, is provided in U.S. Patent Publication No. 20100075327 and U.S. patent application Ser. No. 12/982, 029, filed Dec. 30, 2010, the disclosures of which are incorporated herein by reference in their entireties for all purposes.

In certain embodiments, hybrid assembly is used for error correction within reads of one sequencing technology using the reads from a second sequencing technology. For example, errors within reads from an error-prone, long-read sequencing technology can be corrected using reads from a low-error, short-read sequencing technology. In certain preferred embodiments, such an error correction assembly method is carried out as follows. For an N number of iterations, an alignment is performed using a sequence read from the sequencing technology having a lower raw accuracy (and preferably a longer readlength) and a set of sequence reads from the sequencing technology having a higher raw accuracy. BLASR, described herein, is a preferred alignment method. The alignment output is converted to a SAM file format and SAMTOOLS is used to generate a pileup formatted version of the MSA. The pileup file is used for error correction, and includes the position at which a correction is being made, the number of reads from the "more accurate" sequencing technology that covered that position, the base that was previously present at that position, the type of error correction event (e.g., deletion, insertion, substitution), the corrected base, the consensus base, and the PHRED score of the corrected base. For each read base position recorded in the pileup, the consensus call generated is accepted or rejected according to (a) the number of "more accurate" reads used in determining the consensus call, (b) the percentage of consensus agreement amongst the "more accurate" reads, and (c) the PHRED value of the majority-called base. A summary of the accepted consensus calls is generated and used to create an updated sequence read for the "less accurate" sequencing technology. This updated sequence read is stored and, optionally, subjected to a further iteration of the alignment and error correction method ("correction iteration") to generate a further updated sequence. Once all iterations are complete, an overall summary of all error corrections incorporated into the sequence read from the "less accurate" sequencing technology is generated. In certain embodiments, the pileup step can be optimized by selecting areas within the read to correct rather than correcting the entire read. Selection of such areas can be guided by the results of former correction iterations.

III. De Novo Assembly

Figure 3:
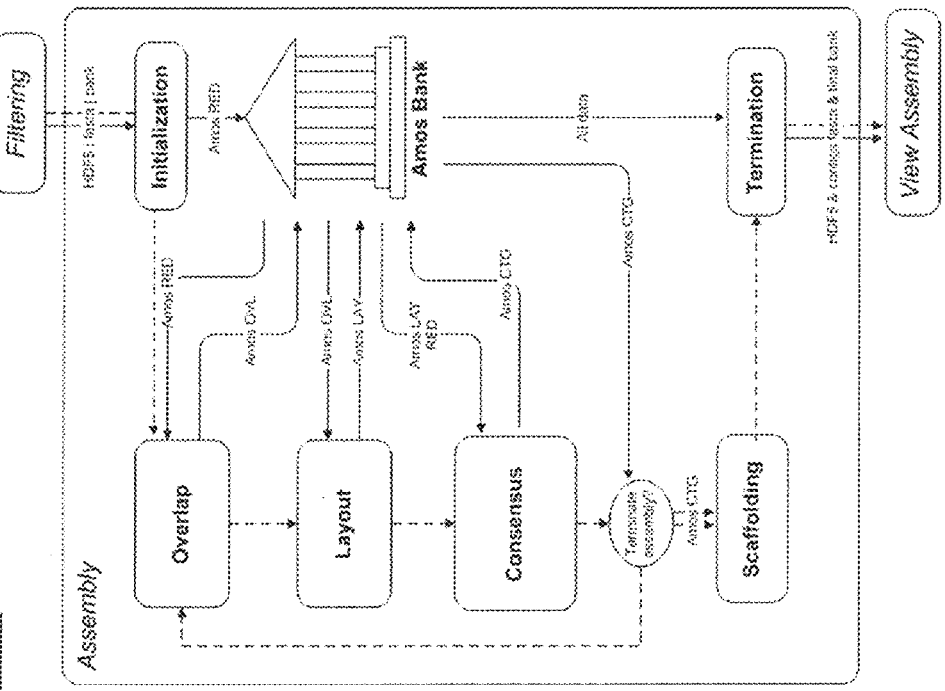
FIG. 3 provides a de novo assembly overview activity diagram.

FIG. 3 provides a diagram depicting a preferred embodiment of a de novo assembly paradigm, including three stages or components of the assembly paradigm: determining overlap between reads, laying out overlapping reads in a linear order by aligning the overlap regions with one another for the set of reads that overlap with at least one other read, and construction of a final consensus from the oriented reads, e.g., as shown in FIG. 2. (See also Pop, M. (2004) Advanced in Computers 60:193-248, incorporated by reference in its entirety for all purposes.) In the overlap component, regions of sequence similarity between sequence reads are identified.

The assembly process assumes that such regions of overlap originate from the same place within the template nucleic acid. Once the overlap regions have been identified, the sequence reads are laid out such that the overlap regions are aligned with one another. Ideally, most or all of the template nucleic acid is represented in the set of sequence reads so aligned. In the consensus stage, a consensus basecall is determined for each position in the template nucleic acid based upon the set of sequence reads that comprise each position. For example, where all basecalls are identical over the set of sequence reads, the basecall becomes the consensus basecall. Where there are different basecalls in different sequence reads, a best basecall is determined based on various criteria, including but not limited to the quality of that basecall in each individual sequence read the frequency of each type of basecall over the set of sequence reads. The process can be iterative, e.g., to further refine the consensus sequence. In certain preferred aspects, as further described below, the invention is particularly useful for de novo assembly of sequence reads having a high insertion-deletion rate, e.g., over a 5%, or a 10%, or a 15%, or in some cases up to a 20% error rate. For example, a greedy suffix tree as described below can detect overlaps using sequence reads having accuracies of only about 80%, and algorithms using Bloom filters can detect overlaps using sequence reads having accuracies of only about 85%.

The input to assembly construction is a set of sequence reads generated from a single template nucleic acid sequence (e.g., via redundant sequencing of one or more template molecules and/or sequencing of identical template molecules) and the outputs include a set of pair-wise overlaps, a layout or contig comprising the sequence reads comprising regions represented in the pair-wise overlaps, and a single consensus sequence that best represents the nucleotide sequence present in the original template nucleic acid sequence or the complement thereof. As such, the assembly process generates a set of overlaps, which are used to align a set of sequence reads to form a contig, which can be analyzed to determine a single consensus sequence. The production of a consensus sequence is important for a wide variety of further analyses of the sequence determined for the template, e.g., in identifying sequence variants, performing a functional analysis based upon homology to known genes or regulatory sequences, or comparing it to other sequences to determine evolutionary relationships between different species, subspecies, or strains.

The de novo assembly method shown in FIG. 3 is derived from the AMOS assembler, which is an open-source, whole-genome assembler available from the AMOS consortium (see the world wide web at sourceforge.net/apps/mediawiki/amos/index.php?title=AMOS). This implementation uses a mixture of python and C/C++, as well as SWIG bindings to AMOS libraries. (SWIG is a tool that simplifies the integration of C/C++ with common scripting languages.) In certain embodiments, a filtering step is included between the consensus step and the "terminate assembly" decision, and the Amos CTG typically feeds into this filtering step. In the filtering step, contigs with low coverage or a small number of reads are filtered out because these contigs are typically due to low-frequency error sequences, such as chimeras. Further, in certain preferred embodiments the final scaffolding step is not performed and is replaced instead with the hybrid assembly algorithms described herein.

As previously noted, the de novo overlap detection operation typically comprises a pairwise analysis of the sequence reads in the original data set to determine regions of overlap between pairs of individual reads. This step is computationally expensive, and for large genomes can involve the comparison of millions of individual reads (for potentially trillions of pair-wise comparisons). To make this step practical, sequence assembly algorithms apply rapid filters to determine read pairs that are likely to overlap. For example, various methods of filtering and trimming the data are known and widely used in the art, e.g., vector trimming, quality filtering, length filtering, no call read filtering, low complexity filtering, shadow read filtering, read trimming, end trimming, and the like, many of which are described in DiGuistini, et al. (2009) Genome Biology 10:R95, which is incorporated herein by reference in its entirety for all purposes.

Depending on the sequence-generating methods used, the determination of sequence assembly may also involve analysis of read quality (e.g., using TraceTuner™, Phred, etc.), signal intensity, peak data (e.g., height, width, shape, proximity to neighboring peak(s), etc.), information indicative of the orientation of the read (e.g., 5'→3" designations), clear range identifiers indicative of the usable range of calls in the sequence, and the like. Such read quality may be used to exclude certain low quality reads from the alignment process. Various preferred methods of determining the quality of sequence data are provided in U.S. Provisional Patent Application No. 61/307,672, filed Feb. 24, 2010; and U.S. Published Application No. 20090024331, both of which are incorporated herein by reference in their entireties for all purposes. In some embodiments, not every call in each read is used in the overlap detection process. In some cases, high raw error rates may indicate a benefit to selecting only reads with a high quality (e.g., high certainty). For example, the quality of the calls in each read can be measured and only those identified as "high quality" be used in the alignment process. In some embodiments, a position is not included in the overlap detection operation if at least a portion of the calls for that position in replicate sequences are below a quality criteria. The quality of a given call is dependent on many factors and is typically closely related to the sequencing technology being used. For example, factors that may be considered in determining the quality of a call include signal-to-noise ratios, power-to-noise ratio, signal strength, trace characteristics, flanking sequence ("sequence context"), and known performance parameters of the sequencing technology, such as conformance variation based on read length. In certain embodiments, the quality measure for the observed call is based, at least in part, on comparisons of metrics for such additional factors to metrics observed during sequencing of known sequences. Methods and software for generating sequence calls and the associated quality information is widely available. For example, PHRED is one example of a base-calling program that also outputs a quality score for each call. After the set of pairwise overlaps has been generated, the calls of lower quality may be added back to the alignment, or, optionally may be kept out of the assembly process altogether, or may be added back at a later stage.

Likewise, after a set of pair-wise overlaps has been identified by an overlap-detection method, such as those described herein, each overlap is assigned a score. Scores allow discrimination between correct and incorrect overlaps. Typically a score threshold is set such that a very small number of overlaps that exceed this threshold will be incorrect, and all overlaps below this threshold are ignored. A preferred score would be the results of Smith-Waterman alignment of the two sequences, however, since Smith-Waterman is slow additional embodiments of overlap scoring methods are also provided within the description of certain overlap detection methods of the invention herein.

A common approach to detecting likely overlaps is to search for regions of exact match between the sequence reads, e.g., subsequent to the filtering described above. Depending on the size of the problem and the computational resources available, exact matches can be detected using simple lookup tables, hashing functions, or more complicated structures such as overlapping algorithms such as the suffix tree. Suffix trees have the advantage of rapid creation and query lookup time, (O(n) and O(l), respectively, where n is the size of the database). The major disadvantage of conventional suffix trees is the large amount of memory used by the data structure, on the order of tens of bytes per character for DNA. (See, e.g., Gusfield, D. (1997) "Algorithms on strings, trees, and sequences," Cambridge University Press, New York, N.Y., the disclosure of which is incorporated herein by reference in its entirety for all purposes.) Another difficulty encountered when using conventional suffix trees in that traditional algorithms for querying them are not well-suited to handling errors in the query, particularly insertions or deletion errors. Certain embodiments of the methods of the invention address this problem by modifying traditional suffix tree query algorithms to create a greedy suffix tree overlap algorithm that allows for insertions and deletions, while largely maintaining the suffix tree's desirable creation and query time.

The input to the algorithm consists of two sets of FASTA-formatted sequences, a query and a target. (FASTA format is a widely used text-based format for representing either nucleotide or peptide sequences using single-letter codes to represent nucleotides or amino acids.) A compressed suffix tree is created from the target sequences using standard methods (e.g., Ukkonen's algorithm using source code from Gusfield, D. (1997) "Algorithms on strings, trees, and sequences," Cambridge University Press, New York, N.Y.). Each query sequence is subsequently compared with the suffix tree using a greedy algorithm, such as the one specified below. In general, a greedy algorithm attempts to find the shortest common supersequence given a set of sequence reads by calculating pairwise alignments of all sequence reads; choosing two reads with the largest overlap; merging the two chosen reads; and repeating the steps until only one "merged" read remains. The algorithm returns matches that obey two user-specified parameters, m the minimum number of matched nucleotides, and e the maximum number of errors, where an error is an insertion or deletion between the query and target sequence. For high error rate data, e can be quite large relative to m (e.g., e=35, m=80).

Informally, the greedy algorithm alternates between two modes: in the first mode it attempts to exactly match as much of the query sequence as possible against the target suffix tree; after further exact matches are impossible, the algorithm enters its second mode, which introduces errors in the query sequence (e.g., substitutions, insertions, or deletions). After each introduced error, the algorithm returns to the first mode, greedily attempting to exactly match as much of the (now modified) query sequence as possible. The algorithm continues to alternate between the two modes until it terminates either when it has matched m or more characters from the query, or it has been forced to introduce at least e errors.

The greedy algorithm is not an exhaustive overlap detection algorithm: it will not find all matches that satisfy the constraints m and e. The number of matches returned for a particular query sequence can be increased by starting the greedy algorithm at different positions along the query, for example, every 10 bases. In certain preferred embodiments, the algorithm is used within the context of an iterative assembly, in which overlaps are detected at multiple stages, allowing algorithm to catch overlaps it missed in previous iterations and to avoid generating overly fragmented assemblies.

This algorithm has the ability to detect overlaps in sequences with quite high error rates. For example, for 6000 sequences with a 75% accuracy, the algorithm detects 1076 overlaps, only 52 of which are incorrect (a 5% false discovery rate). Other algorithms yield false discovery rates of 50% or even higher on the same data, rates that would make de novo assembly from these overlaps impossible.

In theory, the greedy algorithm presented here could be used with data structures other than the suffix tree. The suffix array is probably the most obvious alternative data structure, but other data structures such as a hash or even lookup tables could be used. As compared to the suffix tree, the suffix array consumes less memory, but has a longer query time. The hash and lookup table-based methods suffer from reduced spatial locality of reference when introducing errors in the sequence. The suffix array provides potentially better locality of reference properties than the suffix tree, with proper caching schemes.

Figure 4:
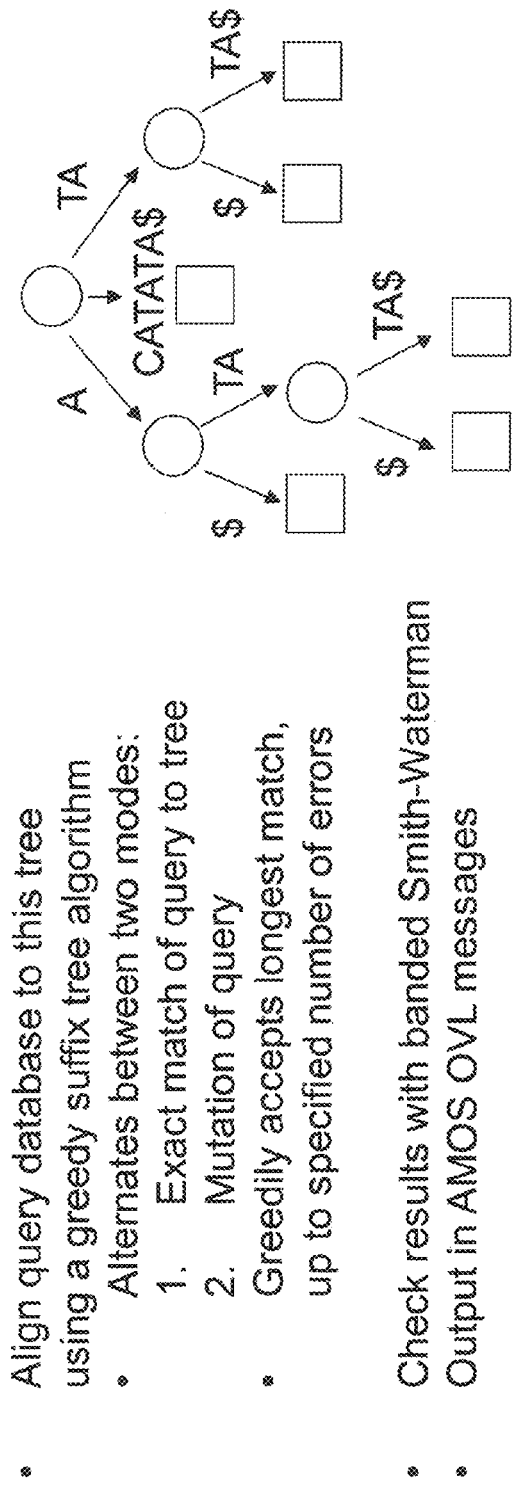
FIG. 4 provides an example of a greedy suffix tree overlap algorithm.

In certain preferred embodiments, the greedy suffix tree overlap algorithm is used during de novo assembly to attempt to map an observed sequence read to a known or candidate target sequence (i.e., generated based upon the sequence reads themselves). In a first step, a suffix tree is constructed from a target database (e.g., FASTA or pls.h5). A query database (database containing the sequence read data) is aligned to this tree using a greedy suffix tree algorithm. The tree alternates between two modes: 1) exact match of the query to the tree; and 2) mutation of query. The algorithm greedily accepts the longest match, which can include up to a specified number of errors. The results are checked with banded Smith-Waterman algorithm, and the results are output in AMOS OVL messages. For example, FIG. 4 illustrates steps to query a sequence CATGTA begin by attempting to match CATGTA to a suffix tree for a target sequence CATATA. Alignment of the query sequence to the suffix tree reveals that CAT matches, but the fourth position does not. The fourth position is mutated, e.g., A>>{C, T, G}. The mutation of A>>G produces a new target sequence GATGTA, which matches the query sequence, resulting in a return hit M=5, E=1 (where M is "match" and E is "error").

In other preferred embodiments, sequence alignment is performed used using an approach of successive refinement to map single molecule sequencing reads. The algorithm used to carry out this successive alignment process is termed a Basic Local Alignment via Successive Refinement (BLASR) algorithm. This algorithm can be understood as having two basic steps: 1) find high-scoring matches of a read in the reference sequence (which may be derived from the sequence reads in de nova assembly) genome, and 2) refine matches until the homologous sequence to the read is found in the reference sequence. The first step involves matching short subsequences or "suffices" of an observed sequence read to a reference sequence using a suffix array (based on short read mapping methods). A suffix array is an index of all suffixes of a string in lexicographic order supporting two operations:

occ("AC")=2
pos("AC")={4, 0}

Current popular short-read aligners use the related and much more compact Burrows-Wheeler Transform (BWT) String for searching. Looking up positions of prefixes using a BWT incurs an extra computational cost: $O(p+occ\ln T)$ versus $O(p\ln T+occ)$ with a suffix array. The suffix array on the human genome requires 17.4 Gb of memory. This can be shared by many threads, so the amortized memory usage is moderate. For every position in a read we find all exact matches for the suffix of the read starting at that position to the genome.

The second step involves several stages. First, high-scoring sets of anchors are found using global chaining (based on whole-genome alignment methods). Next, the resulting putative matches are scored using Sparse Dynamic Programming. Finally, the matches are aligned using a Pair-Hidden Markov Model with quality values in called bases. (See, e.g., Durbin, et al. (1998) Genome Res. 8(3):161-2, incorporated herein by reference in its entirety for all purposes.)

Briefly, each match may be represented as the triplet: (read_pos, genome_pos, length). Global Chaining methods can be used to score matches. Given a set of triples (T):

$$T=\{(start_1,start_2,length)_1, \ldots, (start_1,start_2,length)_n\}.$$

Every interval of length R in the genome is considered, where R is the length of the read. All triples with $start_2$ positions that are with the interval are collected, and an ordered index set $\{i_l, \ldots, i_n\}$ is found such that n is maximal and:

$$start_{1i}+length_{1i}<start_{1j} \text{ and}$$

$$start_{2i}+length_{2i}<start_{2j} \text{ for } i<j\epsilon\{i_1, \ldots, i_n\}$$

This problem can be solved via a variant of Sparse Dynamic Programming. Every interval is assigned a score that is the sum of length values from the triples indexed by the set $\{i_l, \ldots, i_n\}$. The top (highest scoring) max_candidate intervals are retained, where max_candidate is a parameter and typically between 10 and 20 of the highest scoring intervals are retained.

The final two steps are rescoring the top max_candidate intervals with more sensitive alignment routines. Each high-scoring window is realigned using Sparse Dynamic Programming (O(nlogn) runtime). A final set of candidate alignments is scored using a banded affine or Pair-HMM (Hidden Markov Model) alignment. In certain embodiments, reads for a given chromosome can be simulated and errors added with a desired bias toward certain types of errors, e.g., insertions and deletions, e.g. to test the performance of the methods.

Figure 5:
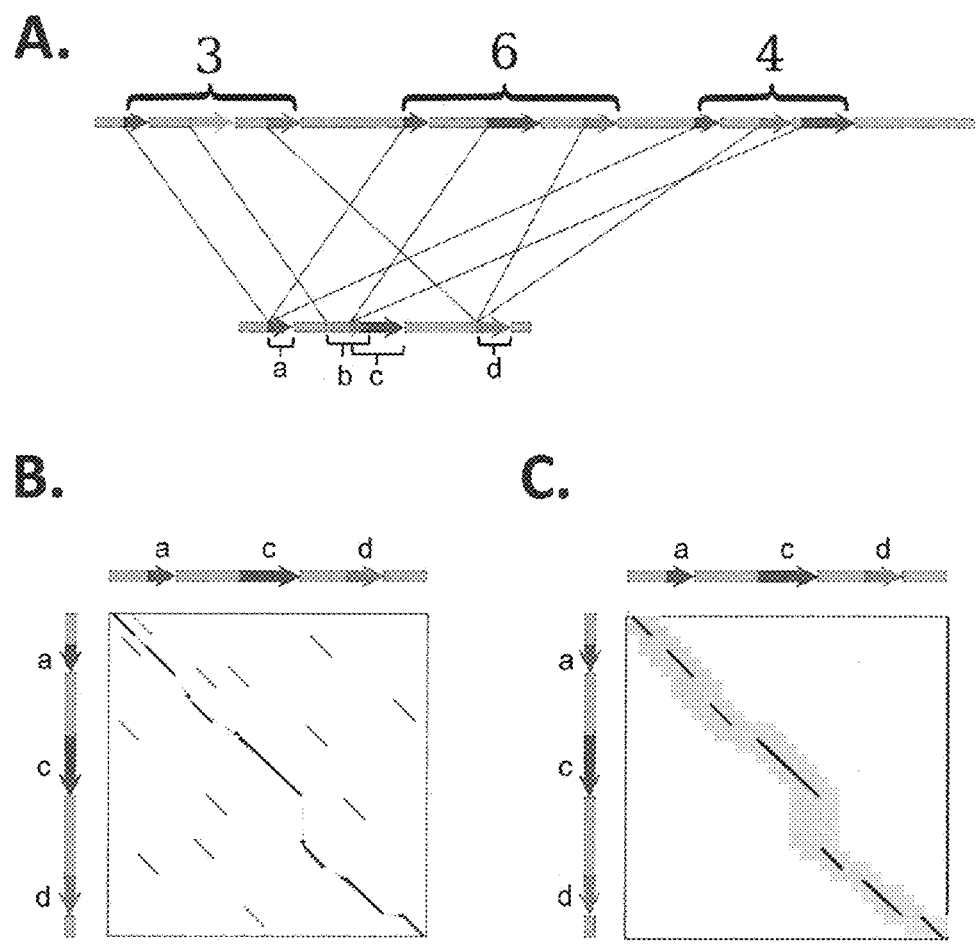
FIG. 5 provides an illustrative overview of the BLASR alignment method. Panel A

The BLASR algorithm can also be conceptualized as operating in three phases: (1) detecting candidate intervals by clustering short exact matches, (2) approximating alignment of reads to candidate intervals using sparse dynamic programming, and (3) detailing banded alignment using the sparse dynamic programming alignment as a guide, as shown in FIG. 5. Read base positions are assigned to reference positions during the third phase of the process.

FIG. 5A depicts candidate intervals found by mapping short, exact matches as shown by arrows a, b, c, and d. Either a suffix array or BWT-FM index of the genome is used to find the exact matches. Intervals are defined over clusters of matches and are ranked; exemplary intervals with score 3, 6, and 4 are shown in FIG. 5. Matches scoring above a threshold are aligned using sparse dynamic programming on shorter exact matches in 5B. In this example, only the interval with a score of 6 surpassed the threshold and was included in the refined alignment. In 5C, alignments having a high-scoring sparse dynamic programming score are realigned using dynamic programming alignment as a guide. A detailed description of the BLASR method is provided below.

Detecting Candidate Intervals.

The input to the BLASR method is a read r with nucleotides $r1, \ldots, r_R$, and a genome g with nucleotides $g1, \ldots, g_G$. All exact matches of substrings from the read and the genome longer than a minimum match length k are found. An exact match may be described as the triplet read position, genome position, and length, or succinctly match a with corresponding functions read(a), genome(a), and length(a) that give the position of the start of the match in the read, start in the genome, and length of the match, respectively. The set of all matches is $\mathcal{A}$.

Either a suffix array or BWT-FM index is used on the genome to query for exact matches, depending on preference for a tradeoff between time and space. The two data structures support the same queries: c=count(r, g), the number of times a query sequence r occurs exactly in a text g, and $\mathcal{P} = \{p_1, \ldots, p_c\}$=locate(q, t), the starting positions of all instances of q in t. Without changing the computational complexity of these queries, they may be modified to answer equivalent queries for counts and locations of the longest common prefix (lcp) between a query and a genome. Let (c, l)=count_lcp(q, t) be the operation that finds the count c and length l of the lcp between q and t. Anchors are located by greedily finding matches slightly shorter than the lcp by 1 to 4 bases between the query and target to increase sensitivity and avoid using anchors that erroneously end in an error. The minimum length anchor that is allowed is of length k, where k is ≥1, preferably between 8 and 15. For example, in many applications, k=12. To build $\mathcal{A}$, scanning across all positions in a read i∈1, . . . , R−k, one computes (c, $l_i$)=count_lcp($r_{i, \ldots, R}$, g) and $\mathcal{P}_i$=locate($r_{i, \ldots, i+l_{i,e}}$, g), and then for all positions $p_j^i \in \mathcal{P}^i$ include in $\mathcal{A}$ a match a with read (a)=i, genome(a)=$p_j^i$, and length (a)=$l_i$. A parameter max count is chosen, and this parameter is the maximum number of times a match is allowed to appear to generate an anchor. Positions mapped when $|\mathcal{P}_i|$>max_count, or short matches when $l_i$<k are excluded.

Descriptions of the implementation and methods for the count and locate queries using suffix arrays are provided in Myers, et al. (Suffix arrays: A new method for on-line string searches, SIAM Journal on Computing, 22:935-948, 1993). Similar descriptions for the SWT-FM index are in Ferragina, et al. (Opportunistic data structures with applications. In Proc. of the 41st IEEE Symposium on Foundations of Computer Science, pages 390-398, 2000) and Langmead, et al. (Ultrafast and memory-efficient alignment of short DNA sequences to the human genome. Genome Biology, 10:R25, 2009). In preferred implementations, the suffix array performs count(q, t) in O(q log t) time and locate(q, t) in O(c) time. The BWT-FM index performs count(q, t) in O(q) time, and locate(q, t) in O(c $\log^\epsilon$ t) time. The additional $\log^\epsilon$ t term relates to a subsampling of an index used to speed up the locate query, where $\epsilon$ is proportional to the rate of subsampling. In tests where $C_{max}$ is set to 10000, the locate operation is 2.6 times slower using a BWT-FM index than a suffix array when looking up the positions of 1M random 15 base words from the human genome. Once the set of anchors $\mathcal{A}$ is generated, anchors are clustered using global chaining (Abouelhoda, et al.; A local chaining algorithm and its applications in comparative genomics; Lecture Notes in Computer Science, 2812:1-16, 2003). To do so, $\mathcal{A}$ is first sorted by position in the genome, and then by positions within a read. Next, clusters of anchors are found in intervals roughly the length of the read. To do this (indexing i across all anchors) a list $\mathcal{A}$, is created containing all anchors that end within a span of length R in the genome starting at read($a_i$). Global chaining finds the largest subset of non-overlapping anchors $C_i \subseteq \mathcal{A}$, increasing in read(a) and genome(a) coordinates; read($a_{i+j}$)+length ($a_{i+j}$)≤read($a_{i+j+1}$), and similar for y. For later use in evaluating the mapping quality value of a read, the sum of all length (a) values for all anchors in $C_i$ is recorded for each cluster.

The clusters are ranked according to the sum $\Sigma_{a_j \epsilon C_i} \log(1/freq(a_j))$ where freq($a_j$) is the frequency of the sequence of $a_j$ in the genome. Furthermore, to decrease runtime, a limit of max_candidates is placed on the maximum number of clusters retained at this step. Clusters are maintained in a priority queue, and the top max_candidates are retained. After scanning the genome for intervals containing clusters of anchors, a set of candidate intervals for alignment, $C^1, C^2 \ldots, C^n$ remain, where $\text{rank}(C^1) \leq \text{rank}(C^2) \leq \ldots \leq \text{rank}(C^n)$, and $n \leq \text{max\_candidates}$. Note, the original indexing of clusters by anchor position becomes irrelevant, and so the subscript index notation is dropped for score-ordered clusters of anchors. While limiting the number of clusters retained may miss alignments to repetitive regions, filtering clusters on this frequency-weighted score has shown to be highly discriminative.

Refining Alignments.

Each cluster $C^i$ is used to define an interval to which the read is realigned and rescored using sparse dynamic programming (SDP) (Eppstein, et al. (1992) Sparse Dynamic Programming i: Linear cost functions; J. Assoc. Comput. Mach. 39:519-545). To help describe how the interval is defined, let $a^{FIRST}$ ($a^{LAST}$) be the anchors with least (greatest) read(a) and genome(a) coordinates in $C^i$. The anchors in $C^i$ frequently do not contain the first and last bases in the read, and the actual starting and ending positions of the read are unknown due to insertion and deletion error in the read. Considering δ to be the maximum insertion rate of the instrument, the starting position of the interval aligned from the genome is:

$s = \text{genome}(a^{FIRST}) - (1+\delta)\text{read}(a^{FIRST})$, and ending position:

$f = \text{genome}(a^{LAST}) + (1+\delta)(R - \text{read}(a^{LAST}))$, of length $l_c = f - s$.

The read must be quickly aligned to a candidate interval, even if it is many tens of kilobases long. Similar to the method of anchoring the interval to the genome but on a smaller scale, a set of matches are found between the read and the candidate interval. The matches used in SDP are of a fixed length, $k^{SDP}$, that is much shorter than the minimum match length used in global chaining, typically between 8 and 11 bases. Let $\mathcal{A}^{SDP}$ be the set of anchors of length $k^{SDP}$ that are exact matches between the read and the interval in the genome $g_s, \ldots, g_f$. Sparse dynamic programming finds the largest subset of anchors $C^{SDP} \in \mathcal{A}^{SDP}$ that are of increasing read(a) and genome(a) values.

The SDP alignment does not align all bases in a read, and so it is necessary to realign a final time using banded dynamic programming. For long reads generated with insertions, the size of band used to bound the alignment becomes prohibitively large. The set of anchors $C^{SDP}$ forms a guide for performing a banded dynamic programming alignment where the band follows the layout of the anchors in $C^{SDP}$ as shown in FIG. 5, C. The subset of cells included from full $R \times l_c$ dynamic programming grid include a band of length $b^{SDP}$ centered about the diagonal where there are anchors, as well as a banded alignment of size $b^{drift}$ between anchors where $b^{drift}$ is sufficient to cover the gaps between anchors.

In addition to the base sequences produced by the PacBio RS, a set of quality values describing probability a base was an insertion, a substitution, or preceded by a deletion, as well as the alternative base that was either substituted or deleted are given for every position. Let $\mathcal{I}$, S, $\mathcal{D}$ be the insertion, substitution, and deletion quality value arrays for a read, and to be the deletion and substitution nucleotide arrays. We use these quality values to compute the score of each cell $s_{i,j}$ in the dynamic programming matrix according to:

$$s_{i,j} = \min \begin{cases} s_{i-1,j-1} + \begin{cases} 0 & \text{if } r_i = g_j \\ S_i & \text{if } r_i \neq g_j, \hat{S}_i = g_j \\ \text{mismatch\_prior} & \text{otherwise} \end{cases} \\ s_{i-1,j} + \mathcal{I}_i \\ s_{i,j-1} + \begin{cases} \mathcal{D}_i & \text{if } \hat{\mathcal{D}}_i = g_{j-1} \\ \text{deletion\_prior} & \text{otherwise} \end{cases} \end{cases}$$

Mapping Quality Values.

Due to the repetitive nature of genomes, a read often maps with a high alignment score to many locations. It is informative to calculate the probability that the interval a read is mapped to by an alignment is the correct (homologous) position in the genome. This probability may be interpreted as a mapping quality value Q for an alignment, allowing downstream analysis such as variant calling to filter alignments by quality.

A Bayesian probability technique was presented in (Li, et al. (2008) Genome Research, 18:1851-1858) to compute the mapping quality for short reads with base calling quality values. Using the formulation in Li, et al. and the notation provided herein: given are read r and a position m that is mapped to a sequence g. The posterior mapping probability that a read r is sampled from m is computed as (Equation 1):

$$p_s(m \mid r, g) = \frac{p(r \mid g_{m, \ldots, i+R-1}) p(m)}{\sum_i p(r \mid g_{i, \ldots, i+R-1}) p(i)}$$

where i runs over all positions in the genome. The quantity $p(r|g_{i, \ldots, i+R-1})$ is the probability of observing the read r if the sequence $i, \ldots, i+R-1$ from the genome is read by the sequencer. For reads that include base quality values q, let $q_i$ denote the probability that a base in a read is incorrect. Then $p(r|g)$ may be replaced by $p(r|g, q)$. In Li, et al. (supra), $p(r|g, q)$ is rapidly approximated by summing the quality values of bases that mismatch in the ungapped alignment between r and $g_i, \ldots, i+R-1$. When there are insertions and deletions in the sequence, the value $p(r|q_{i, \ldots, i+R-1})$ may be computed as $p_f(r|g_{i, \ldots, i+R-1}, \mathcal{H})$; this denotes the forward algorithm probability using a pairwise hidden Markov model (Pair-HMM) $\mathcal{H}$ that encodes probabilities for substitution, insertion, and deletion at every position.

The denominator of Equation 1 gives the marginal probability that if sequence from genome g is possessed, read r may be generated. Evaluating this full sum is computationally infeasible even for short reads and ungapped alignments. Since the probability of observing a read given a template sequence drops geometrically with divergence, most positions in the genome do not contribute significantly to the sum. For short reads, the sum is approximated in Li, et al. (supra) as the sum of the probability of the top scoring alignment and all second best alignments.

In BLASR, the mapping quality value is calculated in a similar manner using an approximation of the sum of Equation 1. The sum in Equation 1 is limited to the top max_candidates alignments, and is then scaled by a factor that reflects the limited sample size by aligning only at most max_candidates clusters. In other words, the sum is further scaled by a factor that reflects a probability that a correct cluster is scored given the sample size of the clusters that are scored. When the read is sampled from a unique region of the genome there will be few clusters of high score, and the true cluster will be the top of the cluster priority queue. However, when the read is sampled entirely from a repetitive sequence there will be many high-scoring clusters and it is possible the cluster from the correct interval on the genome does not have high enough score to stay in the priority queue. To account for this, the correct interval in the genome is assumed to correspond to any significantly highly scoring cluster, and the sum in Equation 1 is multiplied by the ratio of the number of significant clusters found in the genome to max_candidates, as long as the number of significantly highly scoring clusters is greater than max_candidates. The significance of a cluster may be measured by comparing the number of anchors in a cluster to the number of anchors expected at the correctly mapped location. The expected number of anchors a read will have when mapped to the correct location is genome independent, and depends only on the error rate, length of the read, and minimum anchor length. A slightly different metric, the number of anchor-bases (the total number of bases in all anchors), is used to measure cluster significance, and this is similarly genome-independent. For practical purposes, the expectation and variance for the number of anchor-bases for a range of feasible accuracies, read lengths, and minimum match lengths are preferably precomputed when using BLASR. The accuracy of the highest scoring alignment is used as a proxy for the true accuracy of the read. Given the accuracy, the length of the aligned sequence, and the minimum match length, the mean $\mu$ and variance_2 for number of anchor bases is looked up, and all clusters with more than $\mu$–2_anchor bases are counted as significant.

In alternative embodiments, algorithms for determining overlaps between sequence data involves identification of small regions of exact matches known as "k-mers" between reads. Without being bound by theory, sequences that share a large number of k-mers are likely to come from the same region of the sequence to be identified, e.g., a genomic sequence. The value of k is the length of the matched region and is typically on the order of 20-30 base pairs. These regions can be found rapidly using data structures such as suffix trees or hash tables. For two overlapping reads to share an exactly k-mer, the two reads must either have low error rates or be sufficiently long to compensate for the high chance of errors. However, for sequencing reads having relatively frequent errors, the method must be modified to allow errors in the k-mers. Previously developed algorithms have used spaced k-mers with "don't care" positions to allow for substitutions as well as to increase sensitivity over contiguous k-mers. Algorithms having such spaced k-mers are described in the art (e.g., Navarro, G. (2001) ACM Computing Surveys 33:31-88; and Farach-Colton, et al. (2007) J. Computer and Sys. Sci. 73:1035-1044, the disclosures of which are incorporated herein by reference in their entireties for all purposes), but these methods are generally inappropriate for sequencing reads having high insertion and/or deletion rates relative to substitution rates.

As such, in certain preferred embodiments, a gapped k-mers technique provides an insertion-deletion tolerant method of detecting potential overlap between reads. Related approaches have been described in the literature; see, e.g., Burkhardt, et al. (2002) Proceedings of the 13$^{th}$ Symposium on Combinatorial Pattern Matching 2373:225-34, incorporated herein by reference in its entirety for all purposes. A simple example of the technique is as follows. When searching for matches to k-mer in a particular read, the algorithm enumerates all k-d-mers that can be created from that k-mer by introducing d deletions. For example, if the original k-mer is ATGC (k=4) and the desired number of deletions is 1 (d=1), the method would produce four 3-mers, each with a missing base or "gap" at one of the four positions in the original 4-mer: TGC, AGC, ATC, and ATG.

An extension of this technique also allows for insertions or substitutions. For substitutions (s), it is sufficient to systematically replace all internal bases of the k-mer with a "don't care" character (e.g., A*GC, AT*C, etc., where * is a wild-card position). Insertions (i) are dealt with similarly, inserting one or more wild-card characters into the internal positions of the k-mer (e.g., A*TGC, AT*GC, ATG*C, ATGC, ATGC, ATG***C, etc.).

An important feature of this technique is that in theory it can allow much longer k-mers than the exact match technique. For small values of i, s, and d (from 1 to 5) and reasonably large values of k ($>14$), the numbers of k+i–d-mers generated from introducing errors is much smaller than the number of possible k+i–d-mers. Mathematically, $$\binom{k}{i} 4^i \binom{k}{s} 3^s \binom{k}{d} \ll 4^{k+i-d},$$

where the expression on the left is the number of k+i–d-mers created from i insertions, s substitutions, and d deletions, and the expression on the right is the number of possible k+i–d-mers. Liberal parameter values (i=2, s=2, d=2, k=24, corresponding to a 25% error rate), yield a ratio of $1.2 \times 10^{19}$ which would mean a k-mer would still be unique in even the largest of genomes. At a certain point, searching for the large number of modified k-mers becomes computationally infeasible, but algorithmic approaches can improve this situation.

There are several free parameters in this technique that can be readily varied or altered to accomplish the main objective. For example, the length of the k-met; the number of insertions, deletions, or substitutions, if any; the data structure in which the k-mers are found (hash tables, suffix tree, suffix array, or sorted list); and whether gapped k-mers are stored explicitly or merely searched for implicitly in these data structures can be changed or adjusted. The optimal value of each of these parameters is highly dependent on the characteristics of the genome being sequenced and computational resources available for assembly. Nonetheless, the basic idea of using gapped k-mets (as opposed to spaced or exact match k-mers) is maintained.

In certain embodiments, Bloom filters are used in an O(N) algorithm to determine pairs of sequences with matching overlaps in order to decrease the run time and accelerate the analysis. This algorithm may provide greater than 100-fold increases in analysis speed without any significant loss in sensitivity. Specifically, the Bloom filter is used to store the set of all sequence read identifiers from a given analysis for sequences that contain a particular feature. Such an identifier Bloom filter is constructed for every potential feature, and is used to determine candidate read pairs that share a large number of features. In a preferred implementation described herein, the features are the presence or absence of a particular k-mer (gapped or ungapped) in the sequence. Bloom filters were first proposed in Bloom et al. (1970) Communications of the ACM 13(7):422-426, which is incorporated herein by reference in its entirety for all purposes. Further, Bloom filters were used for overlap detection by Malde, et al. (Eleventh International Symposium on Practical Aspects of Declarative Languages; 2008), but Malde's filters do not store identifications as do the Bloom filters described herein.

In preferred embodiments, the algorithm inputs are two files of sequence reads, a query and a target, which can be the same file or two different files. It proceeds in two main stages.

In the first stage, a Bloom filter is created for each possible k-mer. Each Bloom filter contains m bits, where in is on the order of two to ten times the number of sequences expected to possess each feature. The target sequence database is scanned in linear time, processing target sequences in turn. Each sequence identifier is encoded by h hash functions (e.g., h=2), and converted into a value between 0 and m. Subsequently, for each k-mer in the sequence, the h bits corresponding to the hashed values of the sequence identifier are set in that k-mer's Bloom filter. At the end of the first stage of the algorithm, a compact representation of the presence of absence of each k-mer in every read in the target database has been constructed.

In the second stage of the algorithm, the Bloom filters are interrogated using each query sequence, again in linear time. Each query sequence is converted into a set of k-mers, and the Bloom filters for each of these k-mers are subsequently summed. The bits that are set a large number of times in this Bloom filter sum correspond to hashed values for sequence identifiers that share a large number of k-mers with the query sequence. An inverse hash that maps the h hashed values of each sequence identifier can then be used to retrieve the target identifiers for this particular query.

Figure 6:
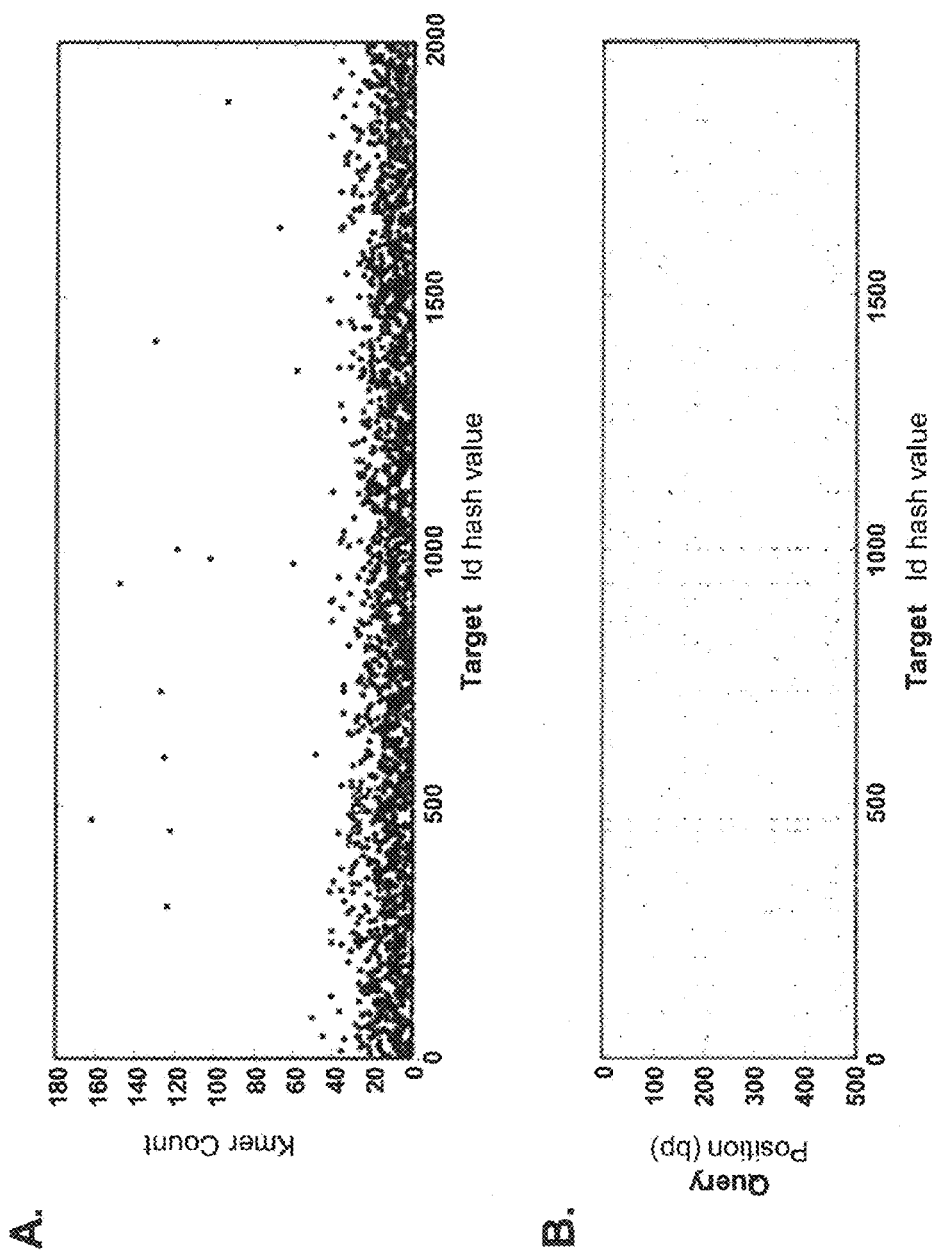
FIG. 6 provides simulated data from an algorithm that uses Bloom filters.

FIG. 6 provides simulated data from the algorithm, and these data demonstrate that summing the Bloom filters for all the k-mers in a particular query sequence yields peaks for target sequences that share a large number of k-mers with the query (the black dots that rise above the noise distribution in panel A). These target sequences are likely to come from the same region of the genome as the query sequence. In FIG. 6, panel B, each horizontal row is a Bloom filter for the k-mer at that position in the query sequence. Each Bloom filter has bits set (black dots) at hash values corresponding to target sequences that contain that particular k-mer.

The above-described algorithm (comprising Bloom filters) has a running time of O(N). In addition, all of the fundamental operations, such as constructing the Bloom filters, querying them, and summing the resulting Bloom filters, can be readily parallelized. Depending on the size of the sequence to be aligned, the identifier Bloom filters may require large amounts of memory during the analysis. For example, for k=8 on a 5× *E. coli* genome, Bloom filters having m=2000 fit in about 1G of memory and yield a false discovery rate of about 5%. Optionally, such an alignment is preferably subsequently checked using a Smith-Waterman alignment algorithm. Larger assemblies (such as the human genome) would require significantly more memory. In general, a target database of size G requires a Bloom filter representation of 2G to 10G. Proper chunking is expected to facilitate the analysis of larger assemblies, e.g., if distributed across multiple nodes.

This algorithm contains at least two free parameters that can be modified while preserving the objective of determining overlap regions between sequence reads. The first is the number of bits stored in each Bloom filter (in). Increasing this value increases the sensitivity of the algorithm, but also increase the memory consumption. The second parameter is the number of hash functions used to encode sequence read identifications (h). This value can be as low as 1 or as high as m−1. Increasing h can either increase or decrease sensitivity, depending on the value of m and the average number of bits set in a particular Bloom filter. Further, there are a much wider family of algorithms that involve using features other than k-mer presence or absence to construct the identifier Bloom filters. Some are closely related to the k-mer concept, but are constructed after the sequence has been transformed in some way. For example, one transformation is to collapse all homopolymers before k-mer identification. Another is to convert all GCs into ones and all ATs into zeroes. A class of features completely unrelated to k-mer presence could summarize the entire sequence in some way, such as using the presence or absence of high GC content. The space of features is infinite, but as long as they can be encoded in an identifier Bloom filter, they can be used with these algorithms.

Figure 7:
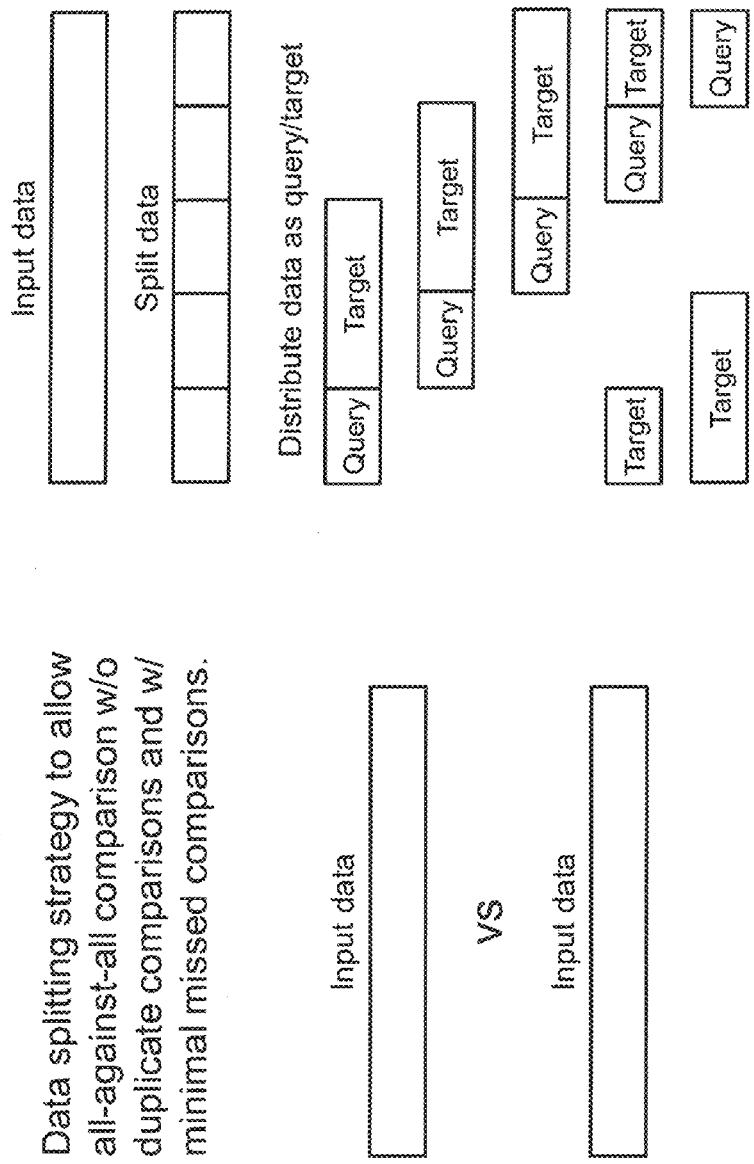
FIG. 7 illustrates a data-splitting strategy.

In certain embodiments, steps are taken to maximize efficiency during the overlap detection operation, e.g., to reduce the occurrence of both duplicate comparisons and missed comparisons. FIG. 7 illustrates an exemplary data splitting strategy that allows all-against-all comparisons without duplicate comparisons and with minimal missed comparisons. Briefly, the overlap detection algorithms described above generally require a "query" and a "target," and so for de novo sequencing the sequence read dataset must provide both. In FIG. 7, the sequence dataset is provided to the algorithm as a plurality of subsets of the input sequence data set ("split data"), and these subsets can be used as the "query" or the "target" in a single pairwise comparison. In certain preferred embodiments, multiple of the subsets are combined to form a larger target for the comparison. By providing a systematic method for providing query and target from the sequencing read dataset, incidences of duplicate or missed comparisons are minimized or avoided altogether.

Figure 8:
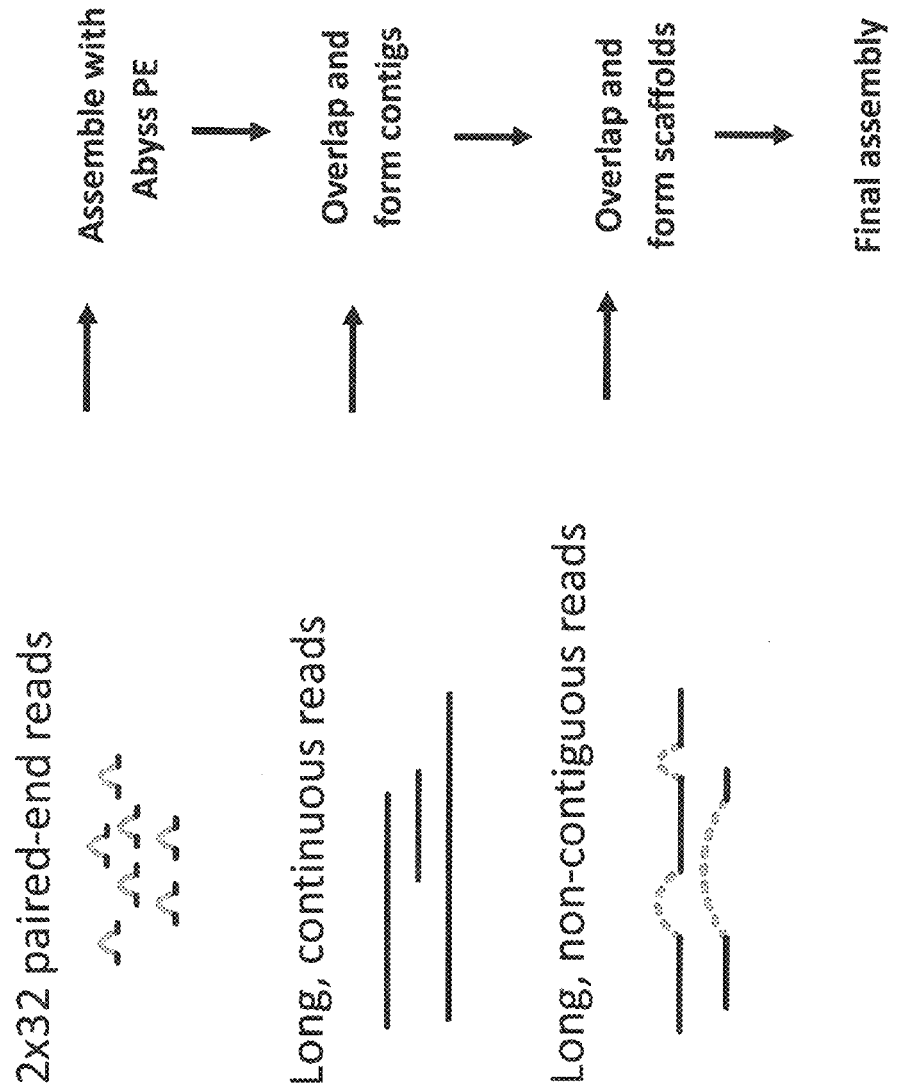
FIG. 8 provides a schematic of the hybrid assembly algorithm used to assemble R. palustris strain DX1.

The exemplary de novo hybrid assembly paradigm provided in FIG. 8 was used to assemble the genome from *R. palustris* strain DX1, and the results for this study are provided in Example 1, herein. The first step was to assemble short paired-end reads from an Solexa sequencing system (Illumina®) using ABySS software, and then combine the assembled paired-end reads with long reads from SMRT™ sequencing. The hybrid assembly of Illumina and SMRT™ sequencing reads was further combined with "strobe" reads, which are long reads comprising non-contiguous subreads. For example, a single strobe read may be 10,000 base pairs in length and have one subread from position 0 to position 2075, a second subread from position 4250 to position 6980, and a third subread from position 8135 to position 10,000. Methods for generating sequencing reads comprising noncontiguous subreads are further described in U.S. Patent Publication No. 2010/0075327 and U.S. patent application Ser. No. 12/982,029, filed Dec. 30, 2010, both of which are incorporated herein by reference in their entireties for all purposes. When the contigs generated with the paired-end and long contiguous read data are further combined with the non-contiguous read data, scaffolds are formed, which are contigs that may comprise gaps with respect to the template nucleic acid, e.g., when none of the sequencing reads covers a particular position or region of the template. Where no basecall can be made at a position in a scaffold, an "N" is assigned to that position. A final assembly is constructed using these three types of sequence reads, and any gaps in the scaffold are represented as one or more "N" basecalls in the final assembly, depending on the number of ambiguous positions in the gap.

Some sequence reads comprise redundant sequence information. For example, a nucleic acid molecule can be repeatedly sequenced in a single sequencing reaction to generate multiple sequence reads for the same template molecule, e.g., by a rolling-circle replication-based method. Alternatively, a concatemeric molecule comprising multiple copies of a template sequence can be subjected to sequencing-by-synthesis to generate a long sequence read comprising multiple complements to the copies. Various preferred methods of generating overlapping sequence reads and redundant sequence information are provided in U.S. Pat. No. 7,476,503; U.S. Patent Publication Nos. 20090298075, 20100081143, and 20100311061; and U.S. patent application Ser. No. 12/982,029, filed Dec. 30, 2010, the disclosures of which are incorporated herein by reference in their entireties for all purposes. When a circular or concatemeric molecule is used as a template for iterative or redundant sequencing, the final sequence read should have a periodic structure. For example, when a circular template is repeatedly processed by a polymerase enzyme, such as in a rolling-circle replication, a long sequencing read is generated that comprises multiple complements of the template, which can be referred to as "sibling reads." However, the periodic pattern can be difficult to identify in certain circumstances, e.g., when using a template of unknown sequence (e.g., size and/or nucleotide composition) and/or when the resulting sequence data contains miscalls or other types of errors (e.g., insertions or deletions).

In some preferred embodiments, the template comprises a known sequence that can be used to align the multiple sibling reads within the overall redundant sequencing read with one another and/or with a known reference sequence. The known sequence may be an adaptor that is linked to the template prior to sequencing, or may be a partial sequence of the template, e.g., where the partial sequence was used to "pull down" a particular region of a genome from a complex genomic sample. By identifying the locations of the alignments between multiple occurrences of the known sequence within the sequencing read, one can infer the periodicity of the read.

In other embodiments, the template does not comprise a known sequence that can be reliably aligned to deduce the periodicity, and so alternative methods are needed to align the sibling reads within the overall read. This can be accomplished by aligning the sequencing read to itself and finding self-similar patterns using standard alignment algorithms, but this method is less successful when the sequencing read contains insertion and/or deletion errors. For example, the Smith-Waterman algorithm focuses on the optimum alignment path and alignment score, which limits its sensitivity for detection periodic sequences with insertion and/or deletion errors. As such, certain aspects of the invention provide methods to improve the sensitivity of an alignment algorithm to identify periodic structure within error-prone or "fuzzy" sequence strings.

In certain preferred embodiments, a whole self-alignment score matrix is used to calculate a quantity that is analogous to the autocorrelation for continuous signal. This autocorrelation function is used to infer periodicity for discrete sequences with high insertion and/or deletion error rates. In other words, the information of the whole self-alignment score matrix is used to estimate the periodicity of the sequence. The method generally comprises four steps. In the first step, the self-alignment scoring matrix is calculated using a special boundary condition, which can be adjusted depending on the known characteristics of the sequencing data and/or the template from which it was generated. The next step is summing over the scoring matrix for all different lags. Third, the peaks are identified and their periodicity used to infer the periodicity of the sequence data. Last, the periodicity of the sequence data is used to guide self-alignment of the sibling reads within the sequence data.

In order to reveal the non-zero offset self-alignment, a special boundary condition is imposed that forces all of the diagonal elements of the scoring matrix to be zero. This prevents the zero-offset self-alignment from contributing to the scoring matrix. Without this boundary condition, the contribution of the zero-offset self-alignment would occlude or "mask out" the non-zero-offset self-alignment, making it far more difficult or impossible to use the significant non-zero-offset alignments to detect the quasi-periodicity of the sequencing.

Figure 9:
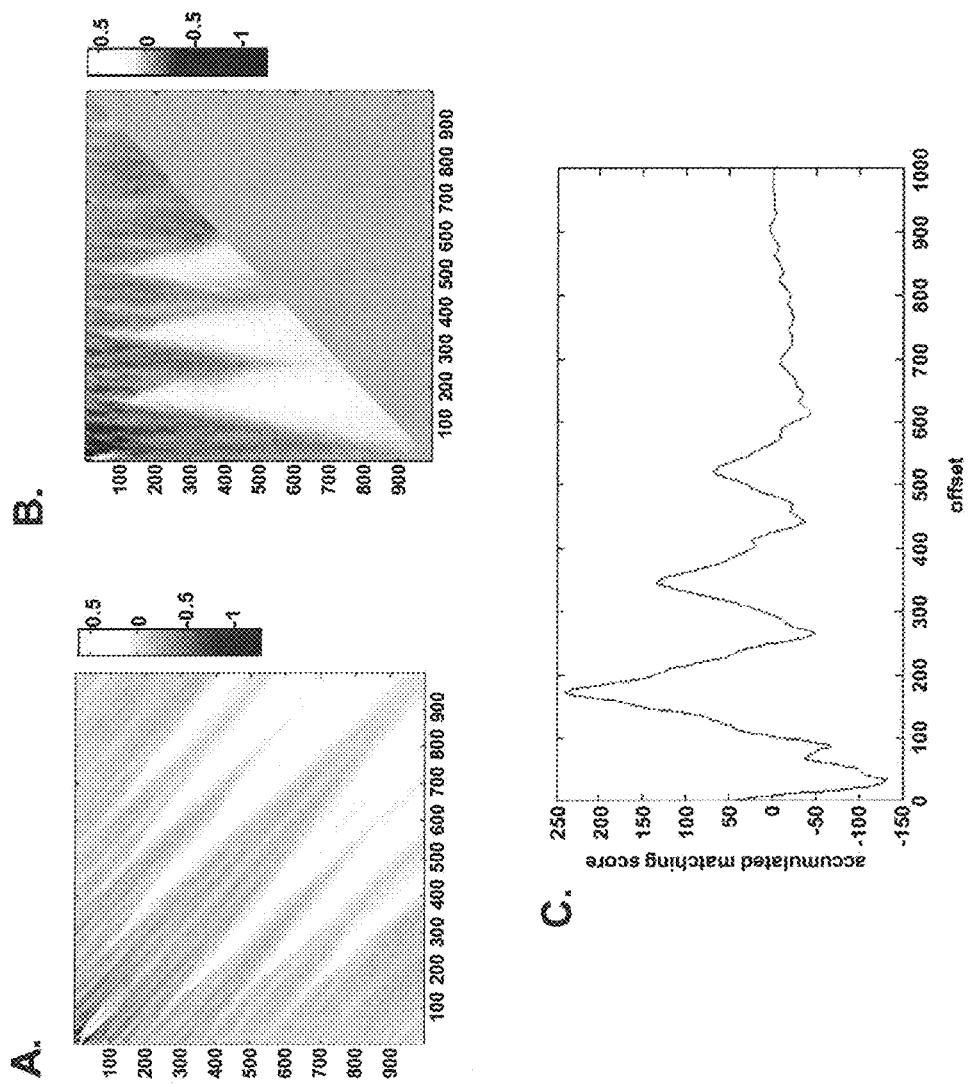
FIG. 9A provides a visualization of an alignment score matrix.
FIG. 9B provides a rotated matrix in which high score ridges are placed in a vertical orientation.
FIG. 9C shows a plot generated by summing the score matrix.

Visualization of the resulting alignment score matrix reveals several diagonal high score "ridges" from a sequence read, as shown in FIG. 9A. By rotating the matrix 45°, the previously diagonal high score ridges are placed in a vertical orientation to provide the plot shown in FIG. 9B. Summing the score matrix over the y-axis provides the plot depicted in FIG. 9C, which shows three easily identifiable peaks that correctly identify the offset of the periodicity of the sequence read. The number of peaks is indicative of the level of redundancy in the sequence read, as well. Optionally, circular templates comprising complementary strands (such as those described in U.S. Patent Publication No. 20090298075) can be used. In such cases, separate alignments can be derived for each of the complementary strands, and these separate alignments can be combined to validate and/or improve the alignments given the known complementarity between the strands.

In certain aspects of the invention, a spatial genome assembler is provided. In traditional methods, sequences are treated as character strings and string-matching techniques are used to identify overlap between reads to combine short reads into longer ones. In contrast, the techniques provided herein map DNA reads into an N-space coordinate system such that any given length of DNA becomes an N-dimensional "thread" through space.

Specifically, given an n-length read of a sequence of bases, B ($b_1 \ldots b_n$), the following function is chosen: $p=F_m(B, i)$, where p is a position in 3-space (x, y, z), m is some integer number of bases smaller than n, and i is some number between 1 and n-m. Applying F to B, a sequence of points is generated: $P=(p_1 \ldots p_{n-m})$ that describes the "thread" of the sequence. If $p_i$ and $p_{i+1}$ are not adjacent to each other, P will not be a thread, so a constraint on F is that any $p_i$ and $p_{i+1}$ must be physically adjacent ($px_i-px_{i+1}$ is in the range $-1 \ldots +1$, as are $py_i-py_{i+1}$ and $pz_i-pz_{i+1}$). An example naïve F could be:

$$F(B,i)=(x=\text{num A's in } b_i \ldots b_{i+m}, y=\text{num C's in } b_i \ldots b_{i+m}, z=\text{num G's in } b_i \ldots b_{i+m})$$

However, this would constrain the "thread space" to be an m by m cube, with most of the thread near position (m/3, m/3, m/3), which would make the approach inadequate for real applications. A better F would perform like a good 3-D hash function, with a more or less even distribution throughout a large thread space.

There are various benefits of this new approach. For example, memory utilization is potentially much more efficient than traditional implementations since only a sparse array of pointers need be kept in RAM. The other data is instead kept on disk. This would facilitate assembly with commodity server hardware. Further, the array of "threads through space" could be made persistent and shared between multiple sequence runs, which is expected to ease implementation of semi-automated comparative genomics methodologies.

Alternative embodiments of the present invention seek to use associations between sibling reads generated from the same template molecule to improve overlap detection for de novo assembly. Some assembly methods combine sibling reads into a single consensus read using a consensus sequence discovery process, in certain preferred embodiments the sibling reads are analyzed without consensus sequence determination, but while still taking into account their relationship as multiple reads of the same template sequence. Although the exemplary method described below focuses on overlap detection for de novo assembly, it can be extended to mapping of reads to a reference sequence or any method that assigns information to a particular sibling read that can be usefully shared among its siblings.

In certain preferred embodiments, summation is used to share overlap score information among sibling reads. In one such embodiment, overlaps are initially called or identified between reads using an alignment algorithm, such as one of those described above. Scores for pairs of reads that belong to the same group of siblings (e.g., were generated from the same template molecule) are combined by summing the scores. This has the effect of combining information across sibling reads, increasing the power of the scoring scheme. Combining overlap scores across sibling reads provides dramatic improvements in the true positive rate, demonstrating that more overlaps are correctly detected, even in the presence of varying error rates and false positive rates. In other embodiments, other methods of combining scores may be used, e.g., max, min, product.

IV. False Overlap Estimation

A problem that has been identified with de nova assembly of sequencing reads is that for large data sets that require a high number of comparisons, the overlap determination step can produce an unacceptable number of false identifications of overlaps, or "false positives," in which regions of the sequence that are similar in sequence space induce incorrect apparent overlaps. The problem is exacerbated when the sequencing reads have a high error rate, e.g., a high insertion-deletion rate.

False overlaps are detrimental to de novo assembly, and can cause misassemblies and fragmentation of the assembly. It is desirable to limit false positives while still detecting a high percentage of true overlaps. There is a standard specificity-sensitivity tradeoff for a fixed size reference sequence at a particular coverage and read accuracy level and a particular overlap scoring scheme. In certain embodiments, a particular score threshold is set at the desired specificity level, thus controlling the number of false overlaps that are detected. However, difficulty arises in that a score threshold that results in a desired (very high) specificity for one size reference sequence or read accuracy will result in a radically different specificity for a different size reference sequence or read accuracy. In general, false overlaps increase quadratically with the size of the reference sequence. Moreover, reads at varying accuracy and length will also affect specificity at a particular threshold in somewhat unpredictable ways. Thus, the exact rate and number of false overlaps can be difficult to predict using score thresholds alone.

In certain aspects of the invention, a more statistically rigorous way to predict false overlaps is provided. To test the method, simulated data was generated from the published $E.$ $coli$ genome sequence at 90% accuracy. An overlap detection algorithm was performed that used a Z-score value to measure the significance of an individual. These Z-scores were converted to p-values using standard statistical techniques, where the p-values referred to the probability of a particular overlap being incorrect. The resulting p-values were corrected for all detected overlaps using the multiple hypothesis testing correction developed by Benjamini and Hochberg (J. R. Statist. Cos. B 57:289-300 (1995)), which converted the p-values into a false discovery rate for a collection of overlaps. The predicted false discovery rate was plotted against the observed false discovery rate, which was known since the data was simulated. Although the correlation was not perfect, it was nearly so in the region of 0.005 to 0.02 false discovery rate, which is typical of allowed false overlap discovery in certain de novo assembly methods using sequence data having a relatively high insertion-deletion rate. As such, this method is useful for prediction the rate of false discovery overlap for a many known overlap detection algorithms used in the art.

V. Consensus Sequence Determination

Multiple sequence alignment (MSA) is a procedure seeking to establish homology relationships between a set of three or more sequences, e.g., nucleotide or amino acid sequences. MSAs are useful because they can be used to construct phylogenetic trees, understand structure-sequence relationships, highlight conserved sequence motifs, and of particular relevance to the sequencing methods provided herein, provide a basis for consensus sequence determination given a set of sequencing reads from the same template. In certain aspects, the present invention provides an MSA refinement procedure using Simulated Annealing and a different objective function than others known in the art (e.g., Sum of Pairs and COFFEE). Certain applications of simulated annealing are described in the art, e.g., in Kirkpatrick, et al. (1983) Science; New Series 220(4598):671-80, incorporated herein by reference in its entirety for all purposes. This objective function not only produces better MSAs, e.g., from nucleotide sequence data, but also has a fairly low computational complexity and is easily implemented. Methods for MSA refinement known in the art may be used in conjunction with the instant invention. For example, see Notredame, et al. (1996) Nuc. Ac. Res. 24:1515-24; Wang, et al. (2005) BMC Bioinformatics 6:200; and Kim, et al. (1994) Cumput. Applic Biosci. 10:419-26, all of which are incorporated herein by reference in their entireties for all purposes.

Figure 10:
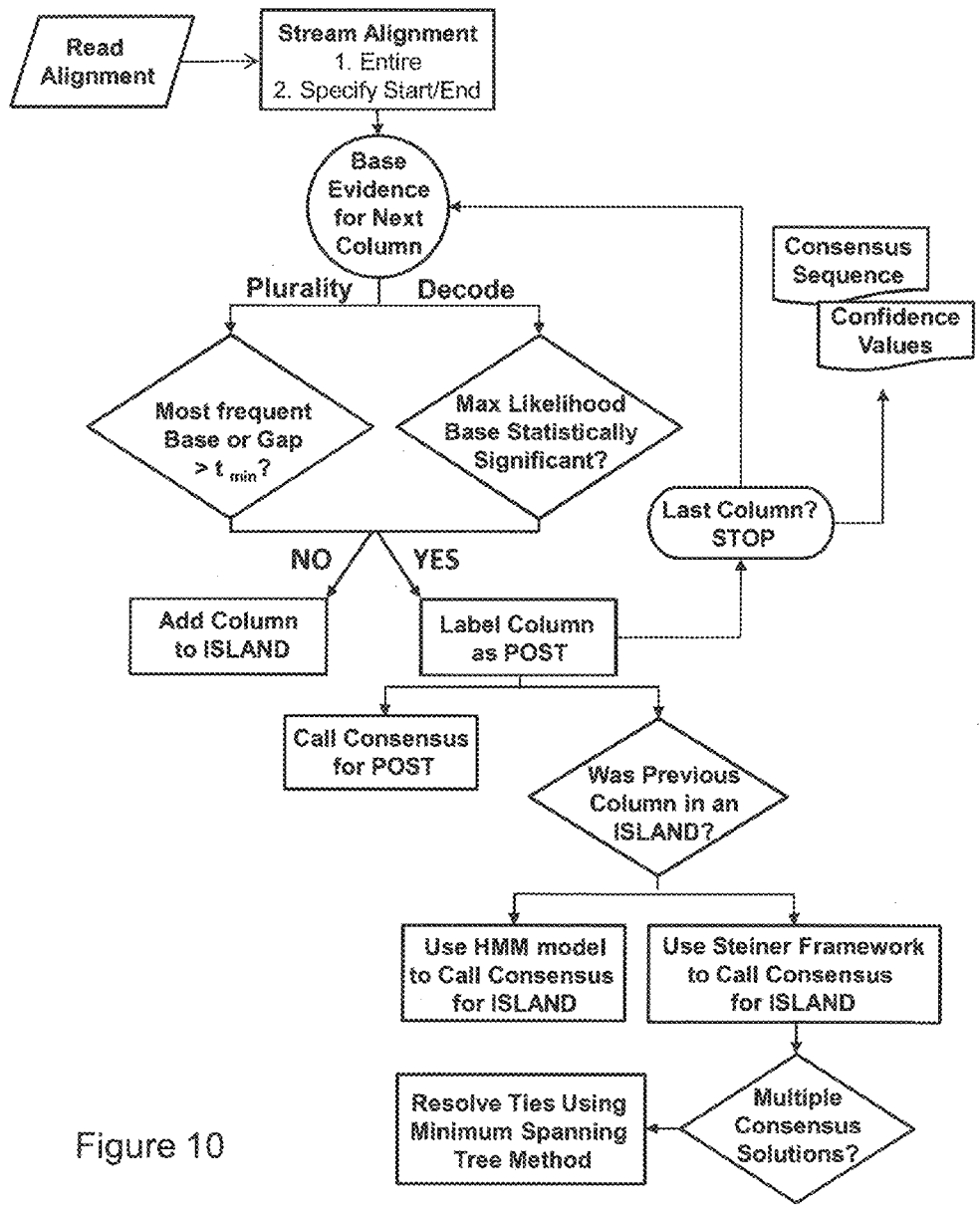
FIG. 10 provides a consensus activity diagram.

FIG. 10 provides a workflow for consensus sequence determination. Various aspects of consensus sequence determination as shown in FIG. 10 are described in detail in U.S. Patent Publication No. 2010/0169026, which is incorporated herein by reference in its entirety for all purposes.

Figure 11:
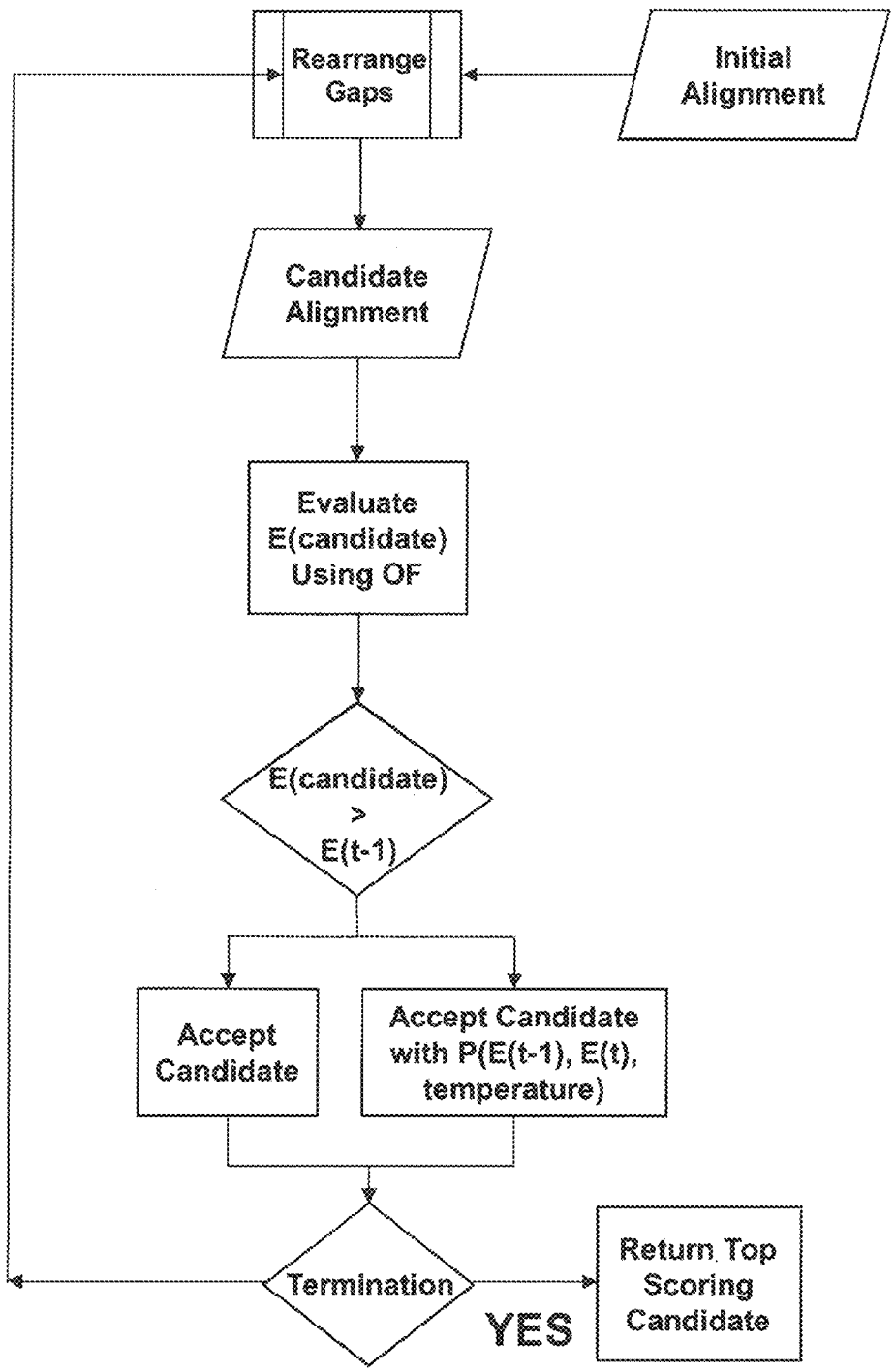
FIG. 11 provides a multiple sequence alignment (MSA) refinement activity diagram.

A preferred embodiment of a simulated annealing framework used to search and evaluate the solution space is shown in FIG. 11. The initial alignment is a close approximation of the optimal solution. Each new candidate alignment is generated by making a local perturbation of the current alignment. Disrupt the alignment by randomly selecting a column in the MSA and performing a gap shifting operation with some probability for each sequence having a gap in that column. Gap shifts can occur to the right or to the left of the current column. Each new candidate is evaluated using the GeoRatio objective function (a geometric ratio objective function), which scores an alignment block as follows:

$$S = |block| \sqrt{\prod_{i=1}^{i=|block|} \frac{\text{Count(most\_frequent\_base\_in\_col}_i)}{\text{Count(2nd\_frequent\_base\_in\_col}_i)}}$$

Effectively, what this scoring mechanism computes is the geometric mean of the signal-to-noise ratio within a column, where a column is a set of "calls" for a given position in the assembled reads. For example, in nucleotide sequence data, a column can be the set of basecalls for a nucleotide position overlapped by a plurality of assembled sequencing reads, where each read provides one of the basecalls. Here, it is important to use the geometric mean as opposed to some other measure such as the arithmetic mean because the desired measure is the percentage of change across two alignments (e.g., one having and one lacking the gap shift), not the absolute magnitude of change. To illustrate this point: an increase of quantity x in the score of a low quality column does not have the same impact on downstream consensus calling as the same increase in the score of a high quality column. It is higher priority to improve low quality columns since those are likely to be miscalled at the consensus level.

The new candidate alignment is accepted if its score is better than the current solution and accepted with some probability if the score is worse. Bad trades are occasionally made in order to prevent the algorithm from sinking into a local optimum. The temperature used at each iteration of the process can be set using an exponential decay function, and the chance with which you would accept a bad solution decreases as the temperature cools. After making the decision to accept or reject the candidate, the process either stops (if termination criteria are met) or proceeds to the next iteration. In certain preferred embodiments, termination criteria are met when n iterations have passed without improvement or after exceeding a predefined number of iterations.

To assess the result of MSA refinement, consensus calling accuracy at low coverage (2-6×) can be compared. The alignment problem is made more difficult and realistic by mutating the reference at every 500th position to a random yet different base. The mutated reference (represents the re-sequencing "reference") is used for read alignment and initial MSA construction, while the original reference (represents the "sample") is used for consensus sequence comparison. This MSA refinement improves low coverage consensus calling.

VI. Computer Implementation

In certain aspects, the methods provided herein are computer-implemented methods, wherein at least one or more steps of the method are carried out by a computer program. In some embodiments, the methods provided herein are implemented in a computer program stored on computer-readable media, such as the hard drive of a standard computer. For example, a computer program for determining at least one consensus sequence from replicate sequence reads can include one or more of the following: code for providing or receiving the sequence reads, code for identifying regions of sequence overlap between the sequence reads, code for aligning the sequence reads to generate a layout, contig, or scaffold, code for consensus sequence determination, code for converting or displaying the assembly on a computer monitor, code for applying various algorithms described herein, and a computer-readable storage medium comprising the codes.

In some embodiments, a system (e.g., a data processing system) that determines at least one assembly from a set of replicate sequences includes a processor, a computer-readable medium operatively coupled to the processor for storing memory, wherein the memory has instructions for execution by the processor, the instructions including one or more of the following: instructions for receiving input of sequence reads, instructions for overlap detection between the sequence reads, instructions that align the sequence reads to generate a layout, contig, or scaffold, instructions that apply a consensus sequence algorithm to generate at least one consensus sequence (e.g., a "best" consensus sequence, and optionally one or more additional consensus sequences), instructions that compute/store information related to various steps of the method, and instructions that record the results of the method.

In certain embodiments, various steps of the method utilize information and/or programs and generate results that are stored on computer-readable media (e.g., hard drive, auxiliary memory, external memory, server, database, portable memory device (CD-R, DVD, ZIP disk, flash memory cards, etc.), and the like. For example, information used for and results generated by the methods that can be stored on computer-readable media include but are not limited to input sequence read information, set of pair-wise overlaps, newly generated consensus sequences, quality information, technology information, and homologous or reference sequence information.

In some aspects, the invention includes an article of manufacture for determining at least one assembly and/or consensus sequence from sequence reads that includes a machine-readable medium containing one or more programs which when executed implement the steps of the invention as described herein.

As will be understood to practitioners in the art from the teachings provided herein, the invention can be implemented in hardware and/or software. In some embodiments of the invention, different aspects of the invention can be implemented in either client-side logic or server-side logic. As will be understood in the art, the invention or components thereof may be embodied in a fixed media program component containing logic instructions and/or data that when loaded into an appropriately configured computing device cause that device to perform according to the invention. As will be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

Figure 12:
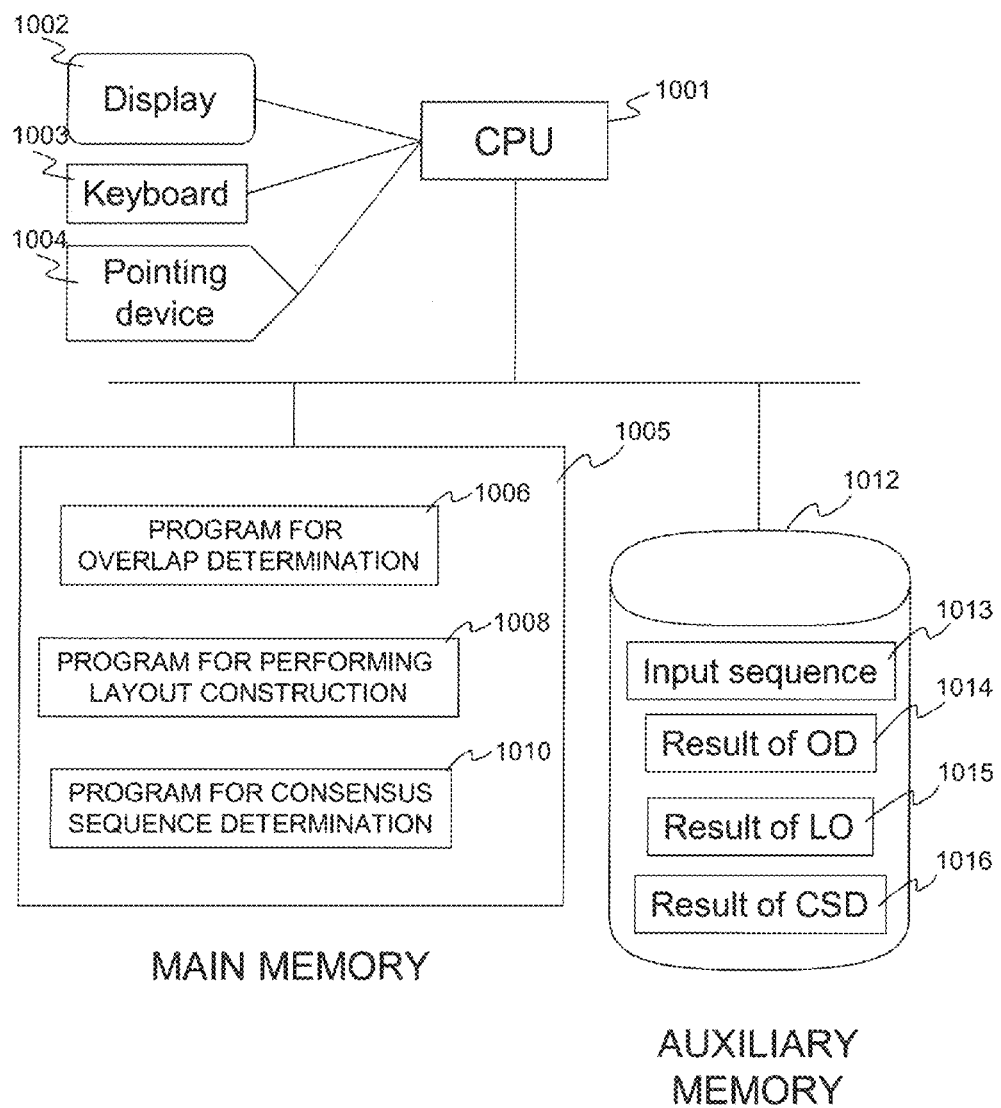
FIG. 12 is a block diagram showing a representative example of a configuration of a device in which various aspects of the invention may be embodied.

One type of an information appliance (or digital device) that may be understood as a logical apparatus that can read information (e.g., instructions and/or data) and use that information to direct server or client logic, as understood in the art, to embody certain aspects of the invention is a computer system as illustrated in FIG. 12. This computer system includes a CPU 1001 for performing calculations, a display 1002 for displaying an interface, a keyboard 1003, and a pointing device 1004, and further comprises a main memory 1005 storing various programs and a storage device 1012 that can store the input sequence 1013, results of overlap detection (OD) 1014, results of layout (LO) 1015), and consensus sequence determination (CSD) 1016. The device is not limited to a personal computer, but can be any information appliance for interacting with a remote data application, and could include such devices as a digitally enabled television, cell phone, personal digital assistant, etc. Information residing in the main memory 1005 and the auxiliary memory 1012 may be used to program such a system and may represent a disk-type optical or magnetic media, magnetic tape, solid state dynamic or static memory, etc. In specific embodiments, the invention may be embodied in whole or in part as software recorded on this fixed media. The various programs stored on the main memory can include a program 1006 to identify regions of overlap between the input, a program 1008 to perform layout construction, and a program 1010 to generate a consensus sequence. The lines connecting CPU 1001, main memory 1005, and auxiliary memory 1012 may represent any type of communication connection. For example, auxiliary memory 1012 may reside within the device or may be connected to the device via, e.g., a network port or external drive. Auxiliary memory 1012 may reside on any type of memory storage device (e.g., a server or media such as a CD or floppy drive), and may optionally comprise multiple auxiliary memory devices, e.g., for separate storage of input sequences, results of alignment, results of layout, results of CSD, results of MSA, and/or other information.

After input sequences and parameters required for the method of the present invention are specified by the display 1002 (also referred to as a "screen"), the keyboard 1003, and the pointing device 1004, the CPU 1001 executes the program stored in the main memory 1005 and overlap detection, layout, and consensus sequence determination are performed by the methods of the present invention. The input sequence 1013 is read from the storage device 1012. The output result of overlap detection (OD) 1014, layout (LO) 1015, and consensus sequence determination (CSD) 1016 can be stored into the storage device 1012. The progress of the various operations in the method of the present invention can be displayed on the display 1002. After completing this processing, the result of the processing can be also displayed on the display 1002, saved to an additional storage device (e.g., ZIP disk, CD-R, DVD, floppy disk, flash memory card, etc.), or displayed and/or saved in hard copy (e.g., on paper). The results of the processing may be stored or displayed in whole or in part, as determined by the practitioner. For example, the results for one or more positions, or one or more pair-wise overlaps, one or more contigs, one or more scaffolds, or one or more consensus sequences may be displayed/saved. These results may further comprise quality information, technology information, alternate (e.g., second or third best) consensus sequences, confidence metrics, etc.

VII. Examples

A. Mapping Benchmarks

Three datasets were generated for evaluating mapping speed and accuracy of different aligners on SMS reads:
 E. coli-PacBio RS E. coli sequenced at 46× coverage by the PacBio® RS sequencer
 E. coli-simulated 46× coverage of reads simulated from E. coli
 H. sapiens 100 MB of reads simulated from the human genome For all E. coli datasets, reads were aligned to the O104 strain (available at ftp://ftp[dot]genomics[dot]org[dot]cn/pub/Ecoli_TY-2482/Escherichia_coli_TY-2482[dot]contig[dot]20110606[dot]fa[dot]gz). In addition, the source reads are available at www[dot]pacbiodevnet[dot]com/DevNetCMSPage as E. coli O42 Raw Reads HDF. Performance was measured additionally with both BLAT and the BWA-SW aligners (Li, et al. (2010) Bioinformatics 26:589-595). BWA-SW was the first mapping method written that used both using the BWT-FM index used in short read mapping and methods that allow mapping long reads with indel error. This method is very compact (under 5 GB of memory for human genome alignments), and very sensitive to mapping reads with indel error compared to other existing methods. BLAST is not included because it was not sufficiently more sensitive than BLAT. All methods we tested were designed for short reads or reads with very few insertions and deletions.

The E. coli-PacBio RS dataset contains 329,825 reads for a total of 213.4 M bases, with lengths and error rate shown in FIG. 1. The sequencing error is composed of 10.7% insertion, 4.3% deletion, and 0.9% substitution, though the details are sensitive to alignment penalty parameters. A summary of the mapping statistics from each of the three programs is shown in Table 1. All programs were executed on a single core of a 2.9 GHz Xeon processor.

TABLE 1

A comparison of the BLASR, BWA-SW, and BLAT methods to align 45x coverage of reads from E. coli to the reference NC_000913.2.

| Method | Number of aligned reads | Number of aligned bases | Runtime |
| --- | --- | --- | --- |
| BLASR | 114350 | 269.1M | 269 m 13.2 s |
| BWA-SW | 123248 | 216.5M | 278 m 1 s |
| BLAT | 99530 | 181.7M | 4724 m 40 s |

To test the sensitivity and specificity of mapping, reads were simulated using an empirical model based on the error profiles of PacBio RS reads aligned to E. coli. The results are shown in Table 2. The methods are largely in agreement on all data, and BLASR is marginally faster. Most of the alignments produced by BWA-SW are split into alignments shorter, possibly overlapping subsequences. We consider the number of bases mapped by BWA-SW as the sum of uniquely mapped bases from each read. For the most part this will not effect mapping and consensus quality, occasionally there are subsequences from reads that are incorrectly mapped while the rest of the read is mapped correctly.

TABLE 2

A comparison of the BLASR and BWA-SW methods reads simulated from E. coli and H. sapiens. The E. coli reads are a simulated counterpart to the reads in 1. Subsequences that are incorrectly mapped by BWA-SW are shown in parentheses.

| Method | Correctly mapped | | Incorrectly mapped | | Missed reads | Filtered reads | Runtime | Memory footprint |
| --- | --- | --- | --- | --- | --- | --- | --- | --- |
| | Reads | Bases | Reads | Bases | | | | |
| E. coli | | | | | | | | |
| BLASR | 109314 | 267.5M | 237 | 0.22M | 1139 | 2526 | 110 m 1 s | 202 MB |
| BWA-SW | 111192 | 261.9M | 1835 | 0.91M | 610 | 2395 | 223 m 57 s | 190 MB |
| H. sapiens | | | | | | | | |
| BLASR | 40729 | 100.9M | 591 | 0.586M | 8 | 1885 | 77 m 37 s | 14.7 GB |
| BWA-SW | 40381 | 96.3M | 292 | 1.16M | 955 | 599 | 105 m 24 s | 4.2 GB |

B. Rhodopseudomonas palustris DX1 Genome

Using algorithms described herein, an assembly of the Rhodopseudomonas palustris DX1 genome was generated using 30× sequencing coverage with significantly longer contig N50s than a comparable assembly using short reads (generated by Illumina® technology) alone. These data demonstrated the value of combining short reads with long reads to further increase N50s. The *R. palustris* assembled contigs were scaffolded using sequence generated by the Pacific Biosciences™ "strobe sequencing" technology—a sequencing protocol which allows the linkage of multiple reads across large distances, in a fashion similar to mate-pair sequencing. Such methods are described in detail in U.S. Patent Publication Nos. 20100075309 and 20100075327, and in U.S. patent application Ser. No. 12/982,029, filed Dec. 30, 2010, all of which are incorporated herein by reference in their entireties for all purposes. The scaffold N50 for the *R. palustris* genome is significantly increased using these reads. This study is described in greater detail below. The combined use of standard long reads and strobe reads shows high promise for simplifying the completion of draft and finished bacterial genomes.

As noted above, a hybrid assembly can be used to select regions of high quality reads from one platform ("A") based on the "higher quality" sequence generated by the other platform ("B"). At least two important questions must be addressed. First, at a particular alignment criteria (parameterized with the number of mismatches for a particular read from platform B), at what rate are reads from platform B expected to recover reads from platform A at a given accuracy (i.e., a true positive rate)? Second, at what rate are reads from platform B expected to hit noise (i.e., a false positive rate)? These questions were addressed by alignment of Illumina® paired-end reads from *Rhodopseudomonas palustris* (a model organism for biofuels) to 5× simulated long, contiguous reads from the same organism. The alignments were performed using the greedy suffix tree algorithm described above. The filtering approached an optimum at about four allowed errors per paired-end read, where there is very little false positive coverage and 40% of the long, contiguous reads were recovered at 20% error (65% for 15% error data). This indicated that the simulated long reads could be de novo filtered with short, paired-end reads, and when performed roughly half of the long, high signal reads were maintained with a minimum of incorporated noise.

Figure 13:
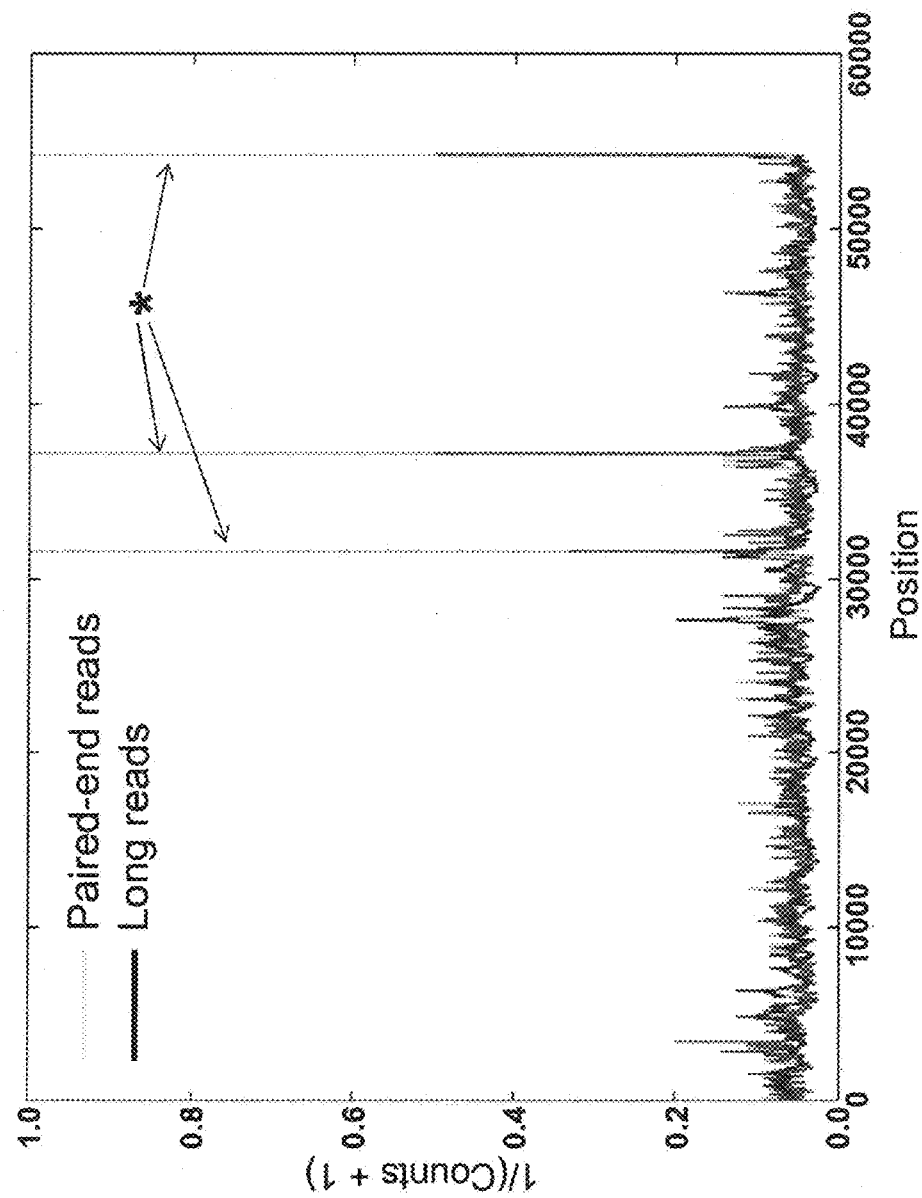
FIG. 13 illustrates an example of hybrid assembly data.

FIG. 13 provides a graphical representation of inverse coverage by Illumina® 2×36 paired-end reads (gray) and Pacific Biosciences™ long reads (black) against Sanger Contig 00036. Peaks in the plot (*) correspond to coverage drops, and therefore correspond to gaps in the Illumina® 2×36 paired-end read contigs.

Figure 14:
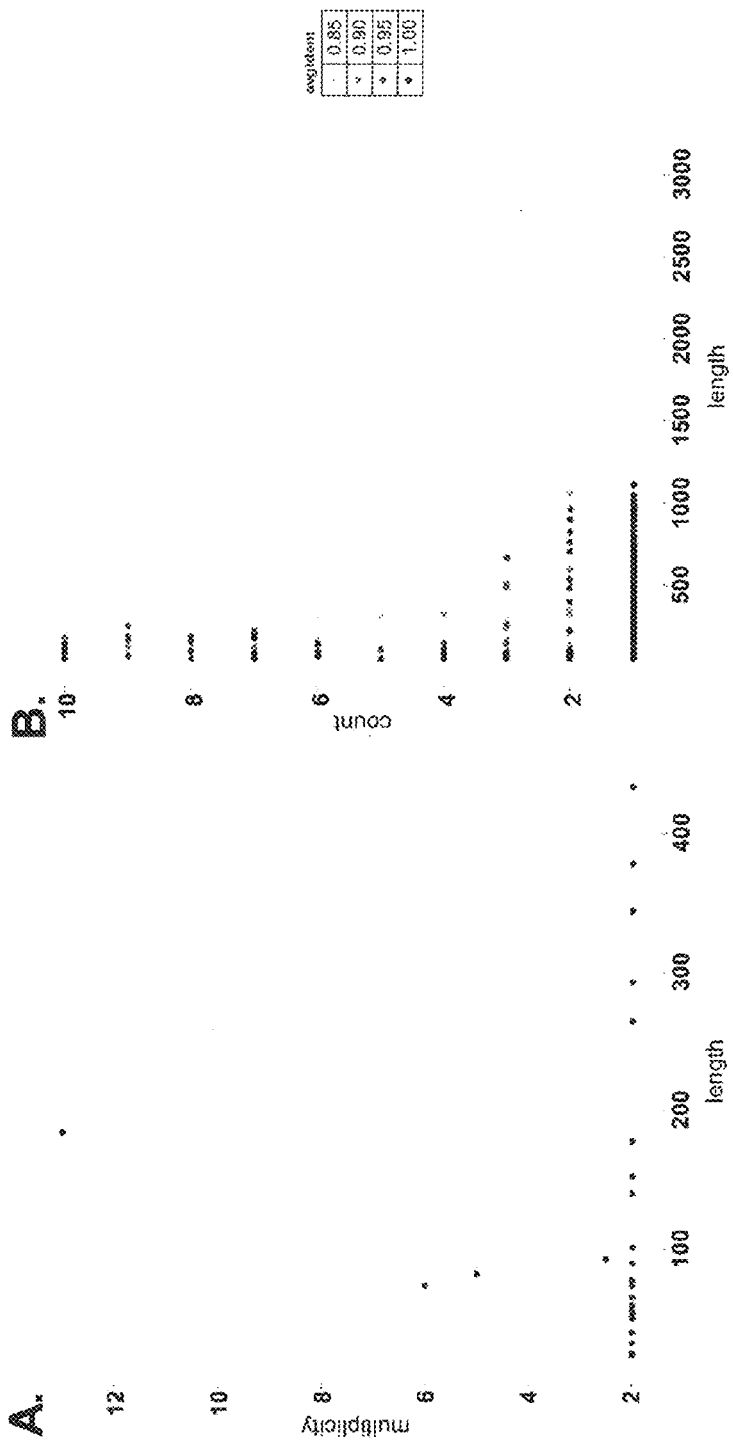
FIG. 14, panels A and B, provide various characterizations of the DX1 genome.
Figure 16:
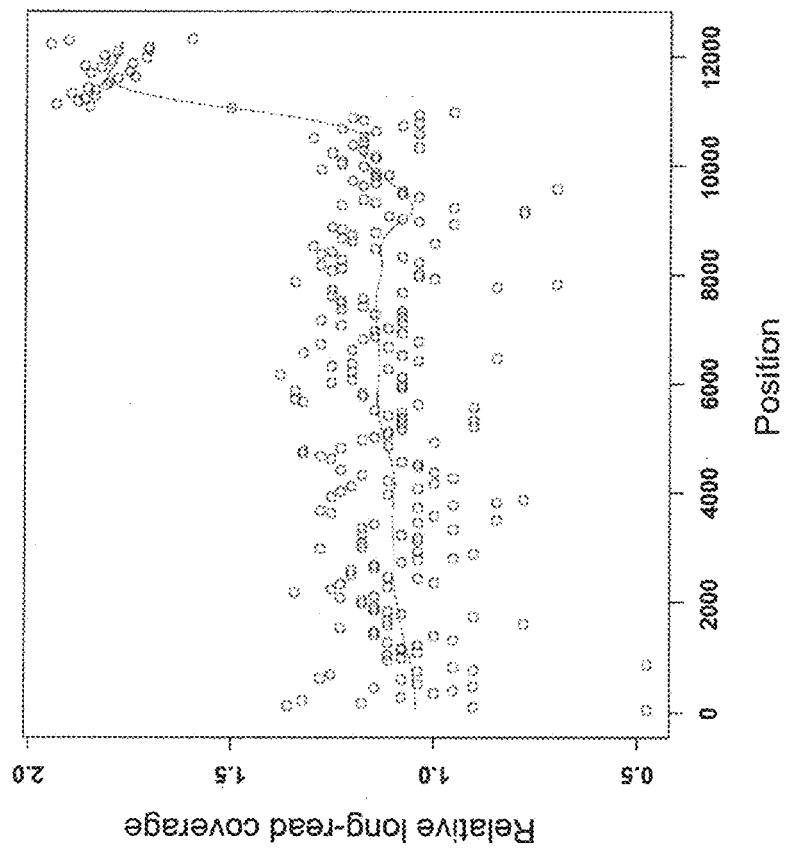
FIG. 16 illustrates identification of repeats in Illumina® contigs using the methods described herein.

FIG. 14A provides a plot depicting the multiplicity of repeats in the DX1 genome; and FIG. 14B provides a plot characterizing the repeat content of the regions in the Sanger reference sequence. FIG. 15 provides a table containing statistics for selected assemblies for contigs greater than 1 kb. The values are provided in base pairs. FIG. 16 illustrates the identification of repeats in the Illumina® contigs based on the elevated coverage in the Pacific Biosciences™ long reads.

Figure 17:
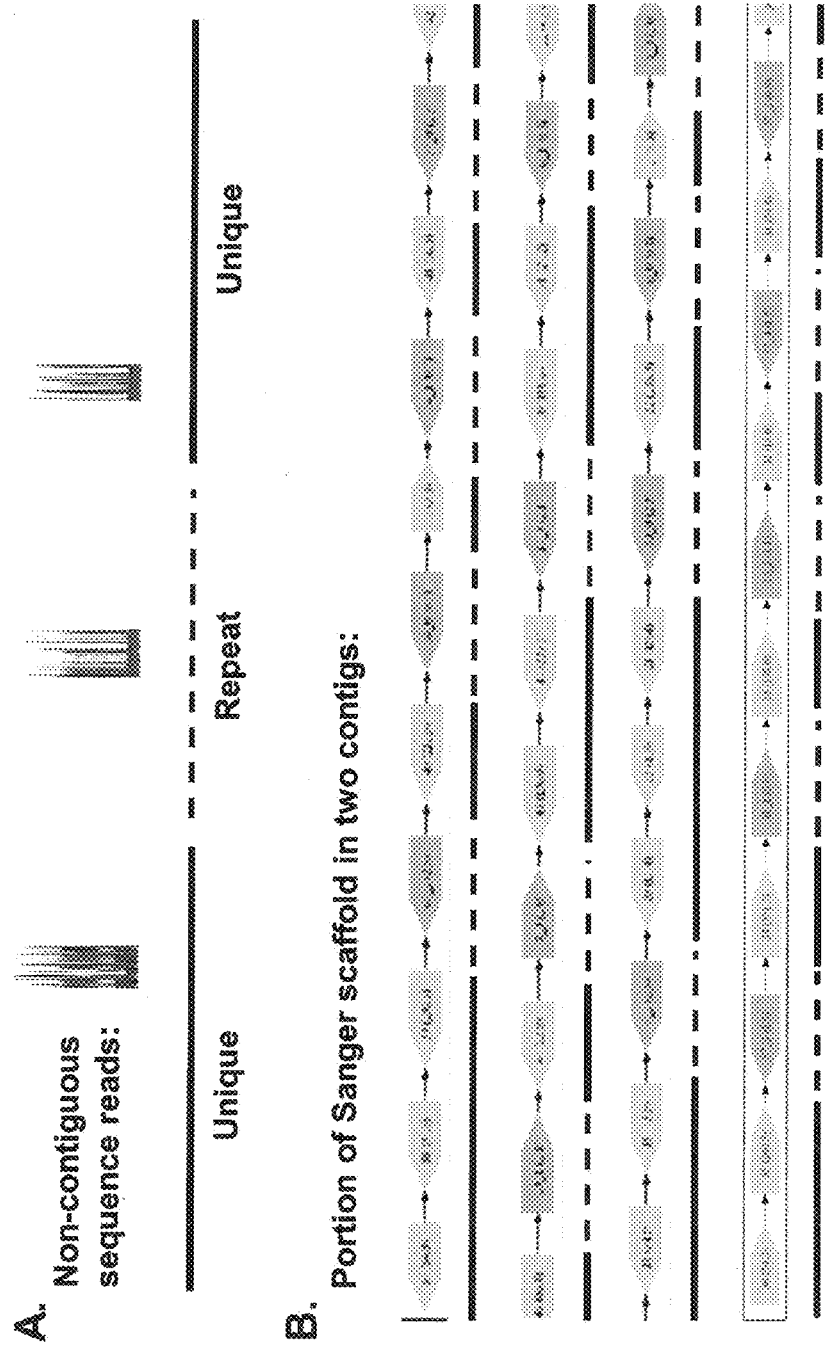
FIG. 17 illustrates scaffolding using a strobe read methodology.

FIG. 17A provides an example of a long, non-contiguous sequence read ("strobe sequence") spanning two Sanger contigs. The finished Sanger contigs are placed into two scaffolds using Pacific Biosciences™ strobe sequences in FIG. 17B. The numbers in parentheses are contig lengths in base pairs. Unique sequence is shown as a solid line, and the repeat regions are hashed lines. Strobe sequencing is further described in U.S. patent application No. 61/139,402, filed Dec. 19, 2008; Ser. No. 12/413,226, filed Mar. 27, 2009; and Ser. No. 12/561,221, filed Sep. 16, 2009, all of which are incorporated herein by reference in their entireties for all purposes.

It is to be understood that the above description is intended to be illustrative and not restrictive. It readily should be apparent to one skilled in the art that various modifications may be made to the different embodiments of the invention disclosed in this application without departing from the scope and spirit of the invention. The scope of the invention should, therefore, be determined not with reference to the above description, but should instead be determined with reference to the appended claims, along with the full scope of equivalents to which such claims are entitled. Throughout the disclosure various references, patents, patent applications, and publications are cited. Unless otherwise indicated, each is hereby incorporated by reference in its entirety for all purposes. All publications mentioned herein are cited for the purpose of describing and disclosing reagents, methodologies and concepts that may be used in connection with the present invention. Nothing herein is to be construed as an admission that these references are prior art in relation to the inventions described herein.

What is claimed is:

1. A method of aligning a sequence read r to a reference sequence g using a minimum match length of k nucleotides, comprising:
    a) obtaining the sequence read r of a target nucleic acid by performing a single molecule sequencing assay, wherein the sequence read r has an insertion-deletion error rate of over 5%;
    b) obtaining the reference sequence g for the target nucleic acid;
    c) determining a set of anchors A, wherein A comprises anchors $\{a, \ldots, a_n\}$, wherein n is a positive integer of two or greater, and wherein each anchor $a_i$ in A comprises (i) a position of a respective subsequence in the sequence read r, (ii) a position of a corresponding portion of the reference sequence g that exactly matches the respective subsequence, and (iii) a length of the respective subsequence in nucleotides, wherein the length of the respective subsequence is k or greater;
    d) clustering $\{a, \ldots, a_n\}$ based on (i) the positions of the corresponding portions of the reference sequence in g and (ii) the positions of subsequences in the sequence read r that are represented by respective $a_i$ in $\{a, \ldots, a_n\}$, thereby obtaining a plurality of clusters $\{C_1, C_2, \ldots, C_m\}$, wherein m is a positive integer of two or greater, and wherein each cluster $C_i$ in $\{C_1, C_2, \ldots, C_m\}$ represents a subset of the anchors A and the anchors $a_i$ in each cluster $C_i$ in $\{C_1, C_2, \ldots, C_m\}$ cluster to a different interval in the reference sequence g;
    e) scoring each respective cluster $C_i$ in $\{C_1, C_2, \ldots, C_m\}$ based on a number of times each subsequence represented by each respective cluster $C_i$ is found in g;
    f) selecting a subset of $\{C^1, C^2, \ldots, C^p\}$ of $\{C_1, C_2, \ldots, C_m\}$ based on a respective score assigned to each cluster $C_i$ in $\{C^1, C^2, \ldots, C^p\}$ by the scoring e), wherein p is a positive integer less than m and wherein $\{C^1, C^2, \ldots, C^p\}$ collectively define a plurality of intervals in g and wherein each $C_i$ in $\{C^1, C^2, \ldots, C^p\}$ represents at least a different interval in the plurality of intervals;
    g) aligning the sequence read r to each interval in the plurality of intervals in g represented by $\{C^1, C^2, \ldots, C^p\}$ using sparse dynamic programming thereby identifying a set of anchors $\{a_1^{SDP}, a_2^{SDP}, \ldots, a_t^{SDP}\}$ in the plurality of intervals in g, wherein t is a positive integer; and
    h) using a banded dynamic programming alignment and the set of anchors $\{a_1^{SDP}, a_2^{SDP}, \ldots, a_T^{SDP}\}$ to align the sequence read r to the reference sequence g.

2. The method of claim 1, wherein the determining c) comprises finding all exact matches from the sequence read r that are longer than the minimum match length k and that exactly match the reference sequence g.

3. The method of claim 2, wherein k is between 8 and 15 nucleotides.

4. The method of claim 1, wherein the determining c) is performed using a suffix array or a BWT-FM index.

5. The method of claim 1, wherein the clustering d) comprises clustering $\{a, \ldots, a_n\}$ using global chaining.

6. The method of claim 5, wherein the clustering comprises sorting $\{a, \ldots, a_n\}$ by position within the reference sequence and within the sequence read and finding a first subset of non-overlapping exact matches that is larger than any other subset of non-overlapping exact matches, wherein the first subset is identified as a cluster $C_i$ clusters $\{C_1, C_2, \ldots, C_m\}$, and the cluster represents an interval in the plurality of intervals.

7. The method of claim 1, wherein the banded dynamic programming alignment comprises aligning all bases in the sequence read to the reference sequence using the set of anchors $\{a_1^{SDP}, a_2^{SDP}, \ldots, a_T^{SDP}\}$ as a guide.

8. The method of claim 1, further comprising calculating a mapping quality value.

9. The method of claim 8, wherein the calculating comprises finding an approximation of the sum of the equation:

$$p_s(m \mid r, g) = \frac{p(r \mid g_{m, \ldots, i+R-1}) p(m)}{\sum_i p(r \mid g_{i, \ldots, i+R-1}) p(i)}$$

wherein, r is the nucleic acid sequence of the target nucleic acid, g is the reference nucleic acid sequence for the reference nucleic acid, m is a position in the reference nucleic acid sequence, $p_s(m|r, g)$ is the posterior mapping probability that r is sampled from position m of g, i is an index to a position in g, R is a nucleotide length of r, $p(r|g_{i, \ldots, i+R-1})$ is the probability of observing r if the sequence $i, \ldots, i+R-1$ from g is read by the obtaining a).

10. The method of claim 1, wherein steps c)-h) of the method are computer-implemented steps.

11. The method of claim 1, wherein at least one of the sequence read, reference sequence, or results from steps c)-h) is stored on a non-transitory computer-readable medium.

12. The method of claim 1, wherein at least one of the sequence read, reference sequence, or results from steps c)-h) is displayed on a screen.

13. The method of claim 1, wherein the single molecule sequencing assay is performed within a zero-mode waveguide.

* * * * *